United States Patent
Takai et al.

(10) Patent No.: US 6,583,324 B2
(45) Date of Patent: Jun. 24, 2003

(54) PROCESS FOR PRODUCING ALDEHYDE

(75) Inventors: Masaki Takai, Kanagawa (JP); Iwao Nakajima, Kanagawa (JP); Tooru Tsukahara, Okayama (JP); Yoshiyuki Tanaka, Kanagawa (JP); Hisao Urata, Kanagawa (JP); Akio Nakanishi, Okayama (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 09/954,171

(22) Filed: Sep. 18, 2001

(65) Prior Publication Data
US 2002/0049355 A1 Apr. 25, 2002

Related U.S. Application Data

(63) Continuation of application No. 09/457,742, filed on Dec. 10, 1999, now Pat. No. 6,291,717.

(30) Foreign Application Priority Data

Dec. 10, 1998 (JP) ............................................. 10-351117
Dec. 14, 1998 (JP) ............................................. 10-354248

(51) Int. Cl.⁷ .......................... C07C 45/50; C07C 29/14
(52) U.S. Cl. ........................ 568/451; 568/454; 568/881
(58) Field of Search ............................... 568/451, 454, 568/881

(56) References Cited

U.S. PATENT DOCUMENTS

| 4,148,830 A | 4/1979 | Pruett et al. |
| 4,482,749 A | 11/1984 | Dennis et al. |
| 4,496,768 A | 1/1985 | Dennis et al. |
| 4,835,299 A | 5/1989 | Maher et al. |
| 5,264,600 A | 11/1993 | Lappe et al. |
| 5,550,302 A | 8/1996 | Mori et al. |
| 5,657,644 A | 8/1997 | Oakey et al. |

FOREIGN PATENT DOCUMENTS

| EP | 0 503 564 A2 | 9/1992 |
| EP | 0 590 611 A1 | 4/1994 |
| JP | 57-123134 | 7/1982 |
| JP | 59-51228 | 3/1984 |
| JP | 59-51230 | 3/1984 |
| JP | 61-501268 | 6/1986 |
| JP | 62-116535 | 5/1987 |
| JP | 62-116587 | 5/1987 |
| JP | 4-290551 | 10/1992 |
| JP | 5-339207 | 12/1993 |
| WO | WO 87/07261 | 12/1987 |

OTHER PUBLICATIONS

Carmela G. Arena, et al., "Mixed phosphito–phosphonato rhodium(I) complexes", J. Chem. Soc., Dalton Trans., pp. 4357–4363, 1996.

*Primary Examiner*—Sreeni Padmanabhan
*Assistant Examiner*—Sikarl A. Witherspoon
(74) *Attorney, Agent, or Firm*—Oblon, Spivak, McClelland, Maier & Neustadt, P.C.

(57) ABSTRACT

A process for producing an aldehyde, which comprises a reaction step of producing an aldehyde by reacting an olefinic compound with carbon monoxide and hydrogen in the presence of a rhodium complex catalyst comprising at least rhodium and an organic phosphite in a reaction zone, a separation step of obtaining a catalyst solution containing the rhodium complex catalyst by separating the aldehyde from a reaction solution taken from the reaction zone, and a recycling step of recycling the catalyst solution into the reaction zone, wherein the aldehyde is separated from the reaction solution in such a manner as to make an aldehyde concentration from 0.5 to 99 wt % in the catalyst solution.

22 Claims, No Drawings

PROCESS FOR PRODUCING ALDEHYDE

This application is a continuation of application Ser. No. 09/457,742 filed on Dec. 10, 1999 now U.S. Pat. No. 6,291,717.

The present invention relates to a process for producing an aldehyde by reacting hydrogen and carbon monoxide with an olefinic compound in the presence of a rhodium complex catalyst containing an organic phosphite as a ligand. Particularly, the present invention relates to a process for preventing a catalyst activity from lowering in recycle use of the rhodium complex catalyst.

Rhodium is widely known as a catalyst for hydroformylation reaction, and it is also known to those skilled in the art that activity and selectivity of hydroformylation reaction can be improved by modifying the catalyst with a ligand such as a trivalent phosphorus compound. Therefore, the trivalent phosphorus compound to be used as a ligand has been variously studied. Particularly, a hydroformylation catalyst containing an organic phosphite exhibiting high reactivity and selectivity as a ligand has been variously studied in recent years.

For example, JP-A-57-123134 discloses a method for using a triarylphosphite having a substituent at a specified position of a phenyl ring as a ligand. JP-A-59-51228 and JP-A-59-51230 disclose a method for using a cyclic phosphite having a phosphorus atom at a bridgehead as a ligand. JP-A-61-501268 discloses a method for using a diorganophosphite having a cyclic structure as a ligand. JP-A-62-116587 discloses a bidentate phosphite compound wherein one of the two phosphite groups has a cyclic structure, and JP-A-62-116535 discloses a bidentate phosphite compound wherein both of the two phosphite groups have cyclic structures. JP-A-4-290551 discloses a method for using a bisphosphite having a cyclic structure as a ligand. Also, JP-A-5-339207 of the present applicant discloses a method for using a bisphosphite or polyphosphite having a substituent at a specified position as a ligand.

However, when industrially using an organic phosphite as a ligand, it is desired to improve its stability.

That is, since rhodium is very expensive, it is desired to recover a rhodium complex catalyst from a reaction product solution for recycle use in the hydroformylation reaction of an olefinic compound using a rhodium complex catalyst containing an organic phosphite. However, when an aldehyde is distilled out by distilling a reaction product solution and a reaction medium containing a rhodium complex catalyst recovered from the bottom of a distillation column is recycled into a reaction zone as a catalyst solution, in accordance with usual method, the catalytic activity is gradually lowered. It is one of the causes that an organic phosphite constituting the rhodium complex catalyst is decomposed and the decomposed product poisons the catalyst or causes further decomposition of the organic phosphite.

The present inventors have studied the lowering of catalyst activity caused by recycling the rhodium complex catalyst in the hydroformylation reaction, and have discovered that an organic phosphite is decomposed to form an organic phosphonate, which poisons the catalyst and becomes a precursor of a compound accelerating further decomposition of the organic phosphite. It has been discovered that the poisoning of the catalyst by this organic phosphonate is easily caused in a separation step and a recycling step, wherein an aldehyde is taken by distilling a reaction product solution of hydroformylation and a catalyst solution containing a rhodium complex catalyst is recovered and recycled into a reaction zone. That is, in such a hydroformylation reaction zone where large amounts of carbon monoxide and hydrogen are present, the organic phosphonate must compete with them to be coordinated with rhodium, and therefore a degree of poisoning the rhodium complex catalyst is relatively little. However, in the separation and recycling steps, carbon monoxide and hydrogen are not present, and therefore the organic phosphonate is easily coordinated with rhodium to lower the catalyst activity.

The present inventors have studied a method for preventing the rhodium complex catalyst from poisoning by the organic phosphonate in the separation and recycling steps, and have discovered that the poisoning of the catalyst can be reduced by separating an aldehyde so as to have the aldehyde remained in the catalyst solution in the separation step. It is considered that the aldehyde in the catalyst solution reacts with the organic phosphonate to convert the organic phosphonate into a compound less poisoning the catalyst.

The present invention has been accomplished on the basis of the above-mentioned discoveries, and according to the present invention, the degradation of the catalyst activity can be prevented by a process for producing an aldehyde, which comprises a reaction step of producing an aldehyde by reacting an olefinic compound with carbon monoxide and hydrogen in the presence of a rhodium complex catalyst comprising at least rhodium and an organic phosphite in a reaction zone, a separation step of obtaining a catalyst solution containing the rhodium complex catalyst by separating the aldehyde from a reaction solution taken from the reaction zone, and a recycling step of recycling the catalyst solution into the reaction zone, wherein the aldehyde is separated from the reaction solution in such a manner as to make an aldehyde concentration at least 0.5 wt %, preferably from 0.5 to 99 wt %, in the catalyst solution.

The present invention is described further in more details hereinafter. The hydroformylation reaction of the present invention can be carried out in accordance with a usual hydroformylation reaction method using a rhodium complex catalyst having an organic phosphite as a ligand.

The rhodium complex catalyst used in the reaction can be prepared in accordance with a well known method of preparing a rhodium-organic phosphite complex catalyst. The rhodium complex catalyst may be previously prepared to be used in the reaction, or may be prepared from a rhodium compound and an organic phosphite in the reaction system. Examples of the rhodium compound used for preparing the catalyst include an inorganic or organic salt of rhodium such as rhodium chloride, rhodium nitrate, rhodium acetate, rhodium formate, sodium chlororhodate, potassium chlororhodate or the like, rhodium metal carried on a carrier such as alumina, silica, activated carbon or the like, a rhodium chelate compound such as rhodium dicarbonyl acetylacetonate, rhodium (1,5-cyclooctadiene) acetylacetonate or the like, and a rhodium carbonyl complex compound such as tetrarhodium dodecacarbonyl, hexarhodium hexadecacarbonyl, $\mu$, $\mu'$-dichlororhodium tetracarbonyl, $[Rh(OAc)(COD)]_2$ (COD represents 1,5-cyclooctadiene), $[Rh(\mu\text{-S-t-Bu})(CO)_2]_2$, or the like.

Examples of the organic phosphite as a ligand include an organic phosphite such as a triarylphosphite, a trialkylphosphite, an alkylarylphosphite or the like. Also, a polyphosphite having a plurality of phosphite structures in the same molecule, such as a bisphosphite, a trisphosphite or the like, can be used.

Among these organic phosphites, a monophosphite can be classified into a compound having a cyclic structure containing a phosphorus atom and a compound not having such a structure. The former monophosphite is expressed by the following formula (1),

  (1)

wherein $R^1$ to $R^3$ are respectively independently a $C_1$–$C_{30}$ hydrocarbon group such as an alkyl group, a cycloalkyl group, an aryl group, an aralkyl group or the like (or a $C_5$–$C_{30}$ heteroaromatic hydrocarbon group), and they may have a substituent which will not inhibit hydroformylation reaction. Examples of these substituents include a halogen atom, a $C_1$–$C_{20}$ alkyl group, a cycloalkyl group, an aryl group, an alkoxy group, an alkylamino group, an acyl group, an acyloxy group, an alkoxycarbonyl group, and the like.

Among these organic phosphites expressed by the formula (1), at least one of $R^1$ to $R^3$ is preferably a substituted aryl group expressed by the following formula (2),

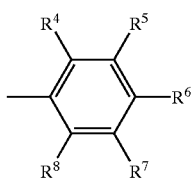  (2)

wherein $R^4$ is an aryl group which may have a substituent that will not inhibit hydroformylation reaction or —$CR^9R^{10}R^{11}$ wherein $R^9$ to $R^{11}$ are respectively independently a hydrogen atom or a hydrocarbon group which may be fluorinated. A preferable example of $R^4$ includes a group having a branched chain at the 1-position such as an isopropyl group or a t-butyl group. $R^5$ to $R^8$ are respectively-independently a hydrogen atom or an organic group which will not inhibit hydroformylation reaction. Also, adjacent groups of $R^5$ to $R^8$ may be bonded to each other to form a condensed aromatic ring or a condensed heteroaromatic ring.

Examples of these organic phosphites include diphenyl(2,4-di-tert-butylphenyl)phosphite, diphenyl(2-isopropylphenyl)phosphite, bis(2-tert-butyl-4-methylphenyl)phenylphosphite, diphenyl(3,6-di-tert-butyl-2-naphthyl)phosphite, bis(2-naphthyl)3,6-di-tert-butyl-2-naphthyl)phosphite, bis(3,6,8-tri-tert-butyl-2-naphthyl)phenylphosphite, bis(3,6,8-tri-tert-butyl-2-naphthyl)(2-naphthyl)phosphite, and the like.

Particularly preferable examples of the organic phosphite expressed by the formula (1) include an organic phosphite wherein all of $R^1$ to $R^3$ are a substituted aryl group expressed by the formula (2). Particular examples of the organic phosphite include tris(2,4-di-tert-butylphenyl)phosphite, tris(2-tert-butyl-4-methylphenyl)phosphite, tris(2-tert-butyl-4-methoxyphenyl)phosphite, tris(o-phenylphenyl)phosphite, tris(o-methylphenyl)phosphite, bis(3,6-di-tert-butyl-2-naphthyl)(2,4-di-tert-butylphenyl)phosphite, bis(3,6-di-tert-butyl-2-naphthyl)(2-tert-butylphenyl)phosphite, tris(3,6-di-tert-butyl-2-naphthyl)phosphite, tris(3,6-di-tert-amyl-2-naphthyl)phosphite, and the like.

Among the monophosphites, a monophosphite having a cyclic structure containing a phosphorus atom is expressed by the following formula (3).

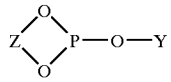  (3)

In the above formula, Z is a divalent hydrocarbon group which may have a substituent that will not inhibit hydroformylation reaction, and Y is a hydrocarbon group or a heteroaromatic hydrocarbon group, which may have a substituent that will not inhibit hydroformylation reaction.

In the above formula (3), Y is preferably a substituted aryl group expressed by the above-mentioned formula (2). Also, Z is preferably an alkylene group, an arylene group or a mixture of the two, which may contain a hetero atom such as oxygen, nitrogen or sulfur atom in a carbon chain. Examples of such a divalent hydrocarbon group include an alkylene group, an alkylene-oxy-alkylene group, an alkylene-amino-alkylene group which may have an alkyl group bonded to a nitrogen atom, an alkylene-thio-alkylene group, a cycloalkylene group, an arylene group, a diarylene group, an alkylene-arylene group, an arylene-alkylene-arylene group, an arylene-oxy-arylene group, an arylene-oxy-alkylene group, an arylene-thio-arylene group, an arylene-thio-alkylene group, or an arylene-amino-arylene or arylene-amino-alkylene group which may have an alkyl group bonded to a nitrogen atom.

A preferable example of the organic phosphite expressed by the formula (3) is expressed by the following formula (4).

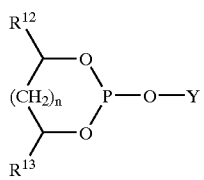  (4)

In the above formula, $R^{12}$ and $R^{13}$ are respectively independently a hydrogen atom or an alkyl group, a cycloalkyl group or an aryl group, which may have a substituent that will not inhibit hydroformylation reaction, and n is an integer of from 0 to 4. Y is as defined in the above formula (3), and is preferably a substituted aryl group expressed by the above-mentioned formula (2).

In the above formula (4), typical examples of $R^{12}$ and $R^{13}$ include a methyl group, an ethyl group, a phenyl group, a tolyl group, a benzyl group, a naphthyl group, a hyroxymethyl group, a hydroxyethyl group, a trifluoromethyl group, and the like.

A preferable example of the organic phosphite expressed by the formula (3) includes one expressed by the formula (5).

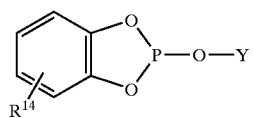  (5)

In the above formula, $R^{14}$ is an alkyl group, a cycloalkyl group, an alkoxy group, an acyl group, an acyloxy group, or an aryl group which may have a substituent that will not inhibit hydroformylation reaction, and its bonding group may be present at any position of o-, m- and p-positions. Also, $R^{14}$ may form a condensed aromatic ring such as a naphthalene ring by condensing with a benzene ring to be bonded. Y is as defined in the formula (3), and is preferably a substituted aryl group expressed by the above-mentioned formula (2).

Another preferable example of the organic phosphite expressed by the formula (3) includes one expressed by the following formula (6).

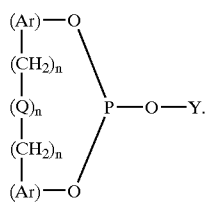

(6)

In the above formula, Ar is an aryl group which may have a substituent that will not inhibit hydroformylation reaction, and may be different from each other. Q is a different crosslinking group such as —$CR^{15}R^{16}$—, —O—, —S—, —$NR^{17}$—, —$SiR^{18}R^{19}$—, —CO— or the like. In these crosslinking groups, $R^{15}$ and $R^{16}$ are respectively independently a hydrogen atom, a $C_1$–$C_{12}$ alkyl group, a phenyl group, a tolyl group or an anisil group, and $R^{17}$ to $R^{19}$ are respectively independently a hydrogen atom or a methyl group. n is respectively independently 0 or 1. Y is as defined in the formula (3). Preferable examples of Y include a $C_1$–$C_{20}$ alkyl or cycloalkyl group such as a methyl group, an ethyl group, a n-propyl group, an isopropyl group, a n-butyl group, a sec-butyl group, a t-butyl group, a n-pentyl group, an isopentyl group, a t-pentyl group, a neopentyl group, a n-hexyl group, a t-hexyl group, a cyclohexyl group, an isooctyl group, a 2-ethylhexyl group, a decyl group, an octadecyl group or the like, and an aryl group such as a phenyl group, an α-naphthyl group, a β-naphthyl group or the like, which may have a substituent that will not inhibit hydroformylation reaction. Examples the substituent of an aryl group include a $C_1$–$C_{20}$ alkyl, cycloalkyl, alkoxy, acyl, acyloxy, alkoxycarbonyl or alkylamino group, or a halogen atom. A particularly preferable example of the organic phosphite of the formula (6) includes one expressed by the following formula (7) or (8).

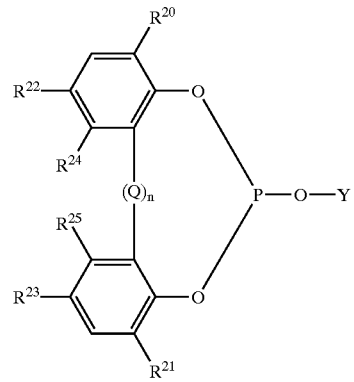

(7)

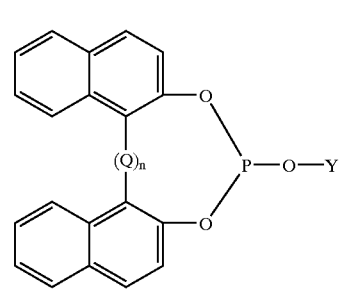

(8)

In the above formulae, Q, Y and n are as defined in the above formula (6), and $R^{20}$ to $R^{25}$ are respectively independently a $C_1$–$C_{20}$ alkyl, cycloalkyl, alkoxy, alkylamino, acyl, acyloxy or alkoxycarbonyl group or a halogen atom.

Some examples of the above organic phosphites having a cyclic structure containing a phosphorus atom are illustrated in the following Table 1.

TABLE 1

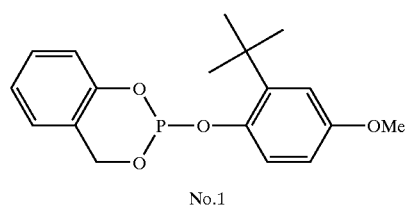

No.1

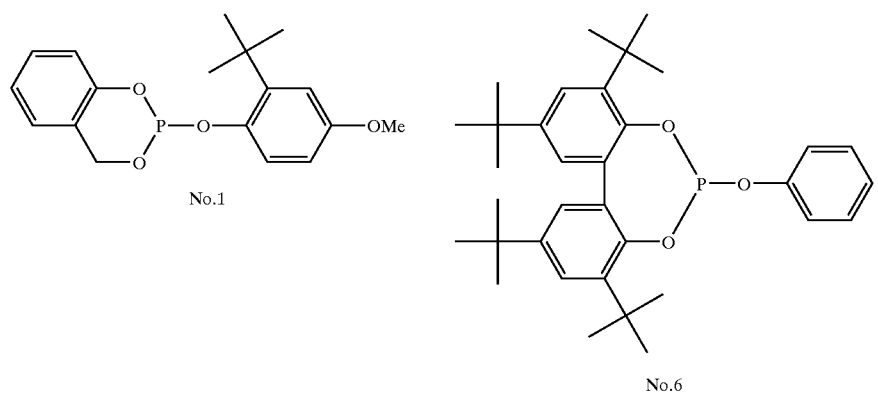

No.6

TABLE 1-continued
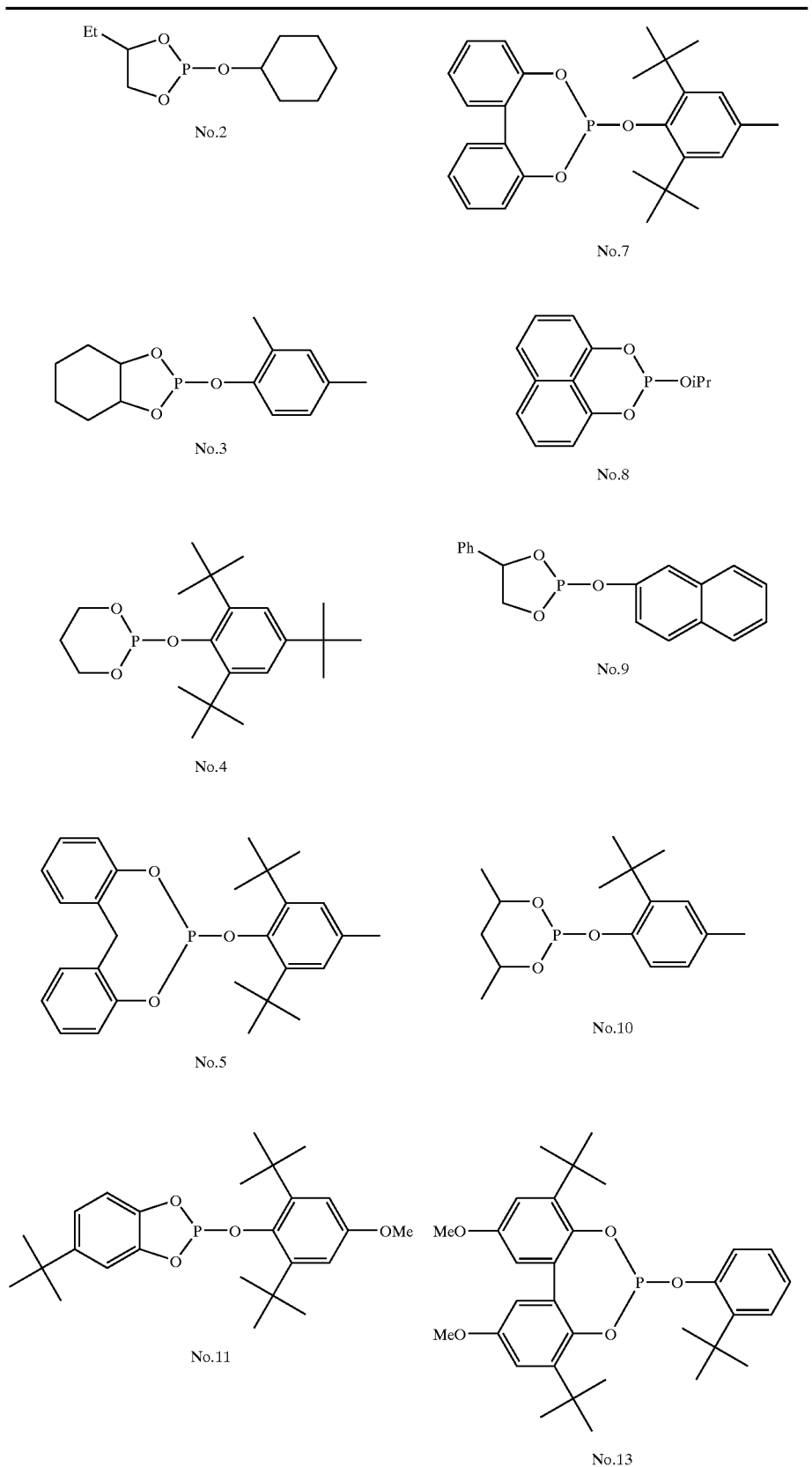

TABLE 1-continued

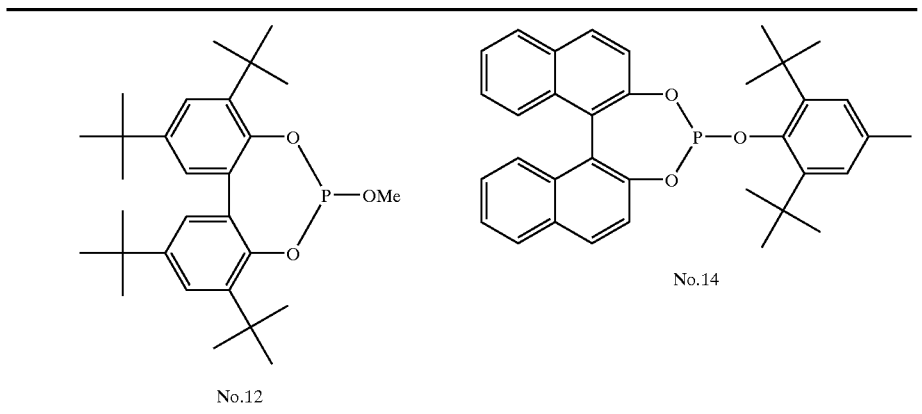

No.12   No.14

A polyphosphite having at least 2 phosphite structures in the molecule used as a ligand in the present invention, is expressed by the following formula (9).

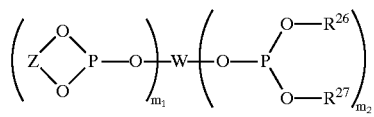

(9)

In the above formula, Z is as defined in the above formula (3), and $R^{26}$ and $R^{27}$ are respectively independently a $C_1$–$C_{30}$ hydrocarbon group such as an alkyl group, a cycloalkyl group, an aryl group, an aralkyl group or the like (or a $C_5$–$C_{30}$ heteroaromatic hydrocarbon group), and these groups may have a substituent that will not inhibit hydroformylation reaction. Examples of these substituents include a halogen atom, a $C_1$–$C_{20}$ alkyl, cycloalkyl, aryl, alkoxy, alkylamino, acyl, acyloxy or alkoxycarbonyl group, and the like, Examples of $R^{26}$ and $R^{27}$ include a $C_1$–$C_{20}$ linear or branched alkyl group such as a methyl group, an ethyl group, a n-propyl group, an isopropyl group, a n-butyl group, a s-butyl group, a t-butyl group, a n-pentyl group, an isopentyl group, a neopentyl group, a t-pentyl group, a t-hexyl group or the like; a $C_3$–$C_{20}$ cycloalkyl group such as a cyclopropyl group, a cyclohexyl group, a cyclooctyl group, an adamantyl group or the like; an aryl group which may have a substituent, such as a phenyl group, an α-naphthyl group, a β-naphthyl group, a methoxyphenyl group, a dimethoxyphenyl group, a cyanophenyl group, a nitrophenyl group, a chlorophenyl group, a dichlorophenyl group, a pentafluorophenyl group, a methylphenyl group, an ethylphenyl group, a dimethylphenyl group, a trifluoromethylphenyl group, a methylnaphthyl group, a methoxynaphthyl group, a chloronaphthyl group, a nitronaphthyl group, a tetrahydronaphthyl group or the like; an aralkyl group such as a benzyl group or the like; and a heteroaromatic group such as a pyridyl group, a methylpyridyl group, a nitropyridyl group, a pyrazyl group, a pyrimidyl group, a benzofuryl group, a quinolyl group, an isoquinolyl group, a benzimidazolyl group, an indolyl group or the like.

W is a ($m_1+m_2$) valent hydrocarbon group which may contain a hetero atom such as oxygen, nitrogen or sulfur atom in a carbon chain and may have a substituent that will not inhibit hydroformylation reaction. $m_1$ and $m_2$ respectively indicate an integer of from 0 to 6, and $m_1+m_2$ indicates an integer of from 2 to 6. When $m_1$ or $m_2$ indicates an integer of at least 2, a plurality of Z, $R^{26}$ and $R^{27}$ may be respectively different from each other.

Z is preferably ones expressed by the above-mentioned formulae (4) to (8), and $R^{26}$ and $R^{27}$ are an aryl group which may have a substituent that will not inhibit hydroformylation reaction. Examples of such an aryl group include a phenyl group, a 2-methylphenyl group, a 3-methylphenyl group, a 4-methylphenyl group, a 2,4-dimethylphenyl group, a 2,5-dimethylphenyl group, a 2,6-dimethylphenyl group, a 2-methoxyphenyl group, a 3-methoxyphenyl group, a 4-methoxyphenyl group, a 2,4-dimethoxyphenyl group, a 2,5-dimethoxyphenyl group, a 2,6-dimethoxyphenyl group, an α-naphthyl group, a 3-methyl-α-naphthyl group, a 3,6-dimethyl-α-naphthyl group, a β-naphthyl group, a 1-methyl-β-naphthyl group, a 3-methyl-β-naphthyl group and the like.

W is preferably an alkylene group or a divalent group expressed by —Ar—$(CH_2)_n$—$(Q)_n$—$(CH_2)_n$—Ar— in the above formula (6). Examples of such a divalent group include a 1,2-ethylene group, a 1,3-propylene group, a 1,3-dimethyl-1,3-propylene group, a 1,4-butylene group, a 1,5-pentylene group, a 1,6-hexylene group, a 1,8-octylene group, a 1,2-phenylene group, a 1,3-phenylene group, a 2,3-naphthylene group, a 1,8-naphthylene group, a 1,1'-biphenyl-2,2'-diyl group, a 1,1'-binaphthyl-7,7'-diyl group, a 1,1'-binaphthyl-2,2'-diyl group, a 2,2'-binaphthyl-1,1'-diyl group, a 2,2'-binaphthyl-3,3'-diyl group, and the like.

Preferable examples of the polyorganophosphite expressed by the formula (9) include a compound wherein Z is a divalent group expressed by —Ar—$(CH_2)_n$—$Q_n$—$(CH_2)_n$—Ar— in the formula (6), $m_1$ is at least 1 and W is expressed by the following formula (10).

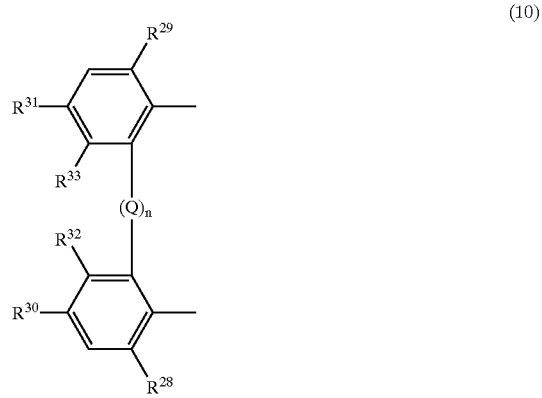

(10)

In the above formula, Q and n are as defined in the formula (6), and $R^{32}$ and $R^{33}$ are respectively independently a $C_1$–$C_{12}$ alkyl, cycloalkyl, alkoxy, silyl or siloxy group, or a halogen atom or a hydrogen atom, examples of which include a methyl group, an ethyl group, a n-propyl group, an isopropyl group, a n-butyl group, a methoxy group, an ethoxy group, a n-propoxy group, a hydrogen atom, a fluorine atom, a chlorine atom, a bromine atom, an iodine atom and the like. Also, $R^{28}$ to $R^{31}$ are respectively independently a $C_1$–$C_{20}$ alkyl, cycloalkyl, alkoxy, silyl or siloxy group, or a halogen atom or a hydrogen atom, example of which include a methyl group, an ethyl group, a n-propyl group, an isopropyl group, a n-butyl group, a t-butyl group, a neopentyl group, a 2,2-dimethylbutyl group, a nonyl group, a decyl group, a methoxy group, an ethoxy group, a t-butoxy group and the like. Also, $R^{30}$ and $R^{32}$ or $R^{31}$ and $R^{33}$ may be bonded to each other to form a condensed ring such as a 1,1'-binaphthyl-2,2'-diyl group or the like.

In the above formula (10), $R^{28}$ and $R^{29}$ are preferably a $C_3$–$C_{20}$ alkyl group having a branched group at the 1-position. Also, $R^{30}$ and $R^{31}$ are a $C_1$–$C_{20}$ alkyl or alkoxy group, or $R^{30}$ and $R^{32}$ or $R^{31}$ and $R^{33}$ may preferably be bonded to each other to form a part of a naphthalene ring which may have an alkyl or alkoxy group as a substituent. Examples of W expressed by the formula (10) include a 3,3'-di-t-butyl-1,1'-binaphthyl-2,2'-diyl group, a 3,3',6,6'-tetra-t-butyl-1,1'-binaphthyl-2,2'-diyl group, a 3,3'-di-t-butyl-6,6'-di-t-butoxy-1,1'-binaphthyl-2,2'1-diyl group, a 3,3'-di-t-pentyl-1,1-binaphthyl-2,2'-diyl group, a 3,3',6,6'-tetra-t-pentyl-1,1'-binaphthyl-2,2'-diyl group, a 3,3'-di-t-butyl-5,5'-dimethyl-1,1'-biphenyl-2,2'-diyl group, a 3,3',5,5'-tetra-t-butyl-1,1'-biphenyl-2,2'-diyl group, a 3,3',5,5'-tetra-t-pentyl-1,1'-biphenyl-2,2'-diyl group, a 3,3'-di-t-butyl-5,5'-dimethoxy-1,1'-biphenyl-2,2'-diyl group, a 3,3'-di-t-butyl-5,5',6,6'-tetramethyl-1,1'-biphenyl-2,2'-diyl group, a 3,3',5,5'-tetra-t-butyl-6,6'-dimethyl-1,1'-biphenyl-2,2'-diyl group, a 3,3',5,5'-tetra-t-pentyl-6,6'-dimethyl-1,1'-biphenyl-2,2'-diyl group, a 3,3'-di-t-butyl-5,5'-dimethoxy-6,6'-dimethyl-1,1'-biphenyl-2,2'-diyl group, a 3,3',5,5'-tetra-t-butyl-6,6'-dichloro-1,1'-biphenyl-2,2'-diyl group, and the like.

The most preferable example of W expressed by the formula (10) is a compound wherein $R^{32}$ and $R^{33}$ are respectively independently a $C_1$–$C_3$ alkyl or alkoxy group or a halogen atom, such as a methyl group, an ethyl group, a n-propyl group, an isopropyl group, a methoxy group, an ethoxy group, a n-propoxy group, an isopropoxy group, a fluorine atom, a chlorine atom, a bromine atom, an iodine atom or the like. Such examples of W include a 3,3'-di-t-butyl-5,5',6,6'-tetramethyl-1,1'-biphenyl-2,2'-diyl group, a 3,3',5,5'-tetra-t-butyl-6,6'-dimethyl-1,1'-biphenyl-2,2'-diyl group, a 3,3',5,5'-tetra-t-butyl-6,6'-diethyl-1,1'-biphenyl-2,2'-diyl group, a 3,3',5,5'-tetra-t-butyl-6,6'-dimethoxy-1,1'-biphenyl-2,2'-diyl group, a 3,3'-di-t-butyl-5,5'-dimethoxy-6,6'-dichloro-,1,1'-biphenyl-2,2'-diyl group, a 3,3',5,5'-tetra-t-butyl-6,6'-difluoro-1,1'-biphenyl-2,2'-diyl group, and the like.

Some examples of the polyphosphite expressed by the formula (9) are illustrated in the following Table 2.

TABLE 2

No. 1

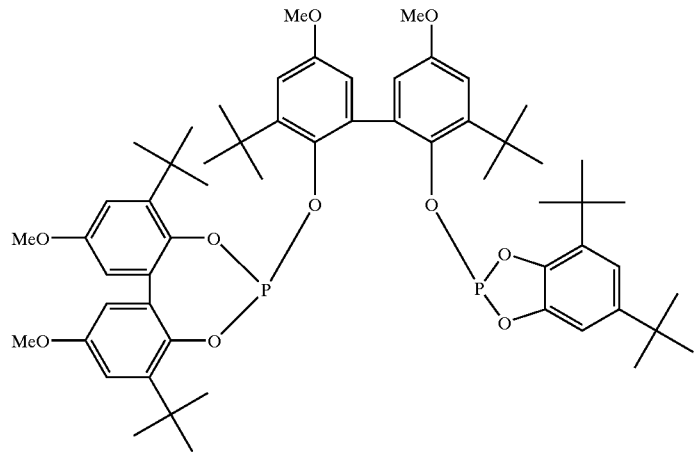

No. 2

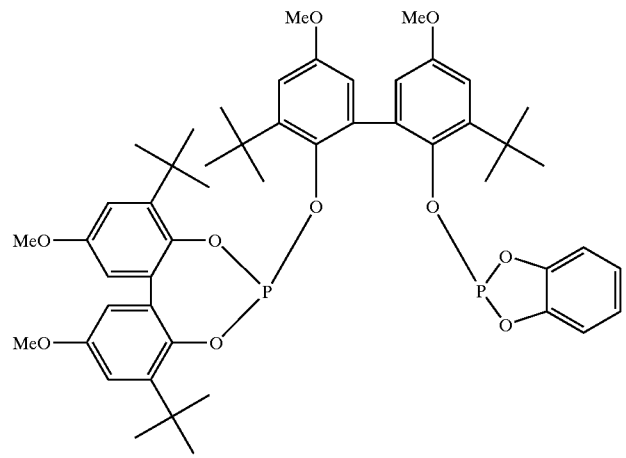

TABLE 2-continued
No. 3
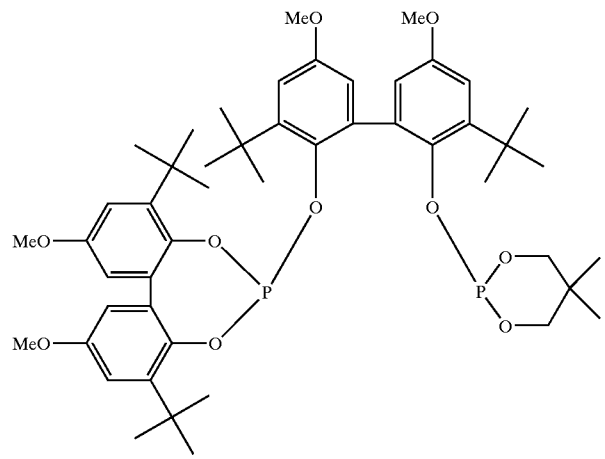
No. 4
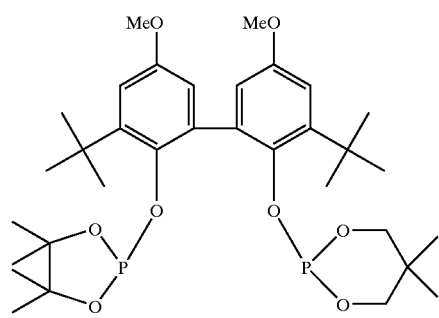
No. 5
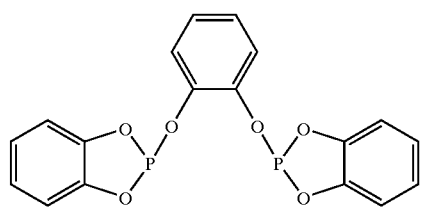
No. 6
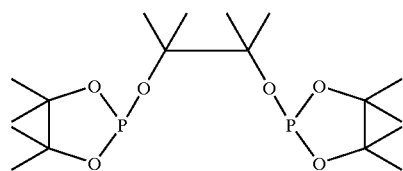
No. 7
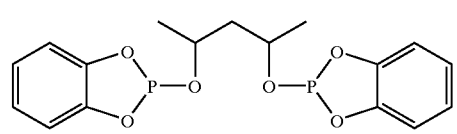

TABLE 2-continued
No. 8
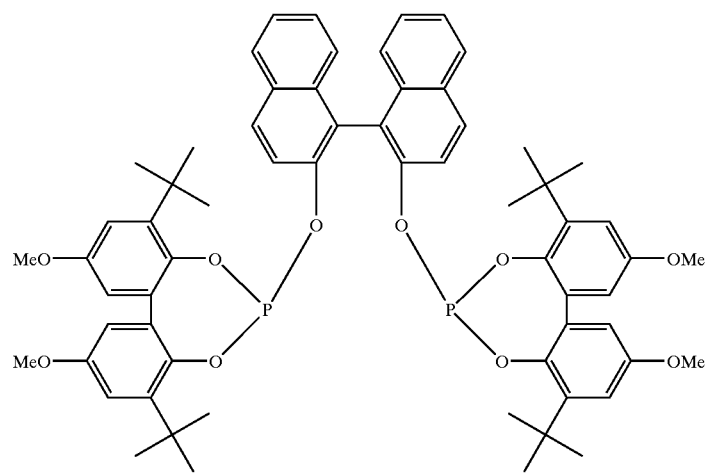
No. 9
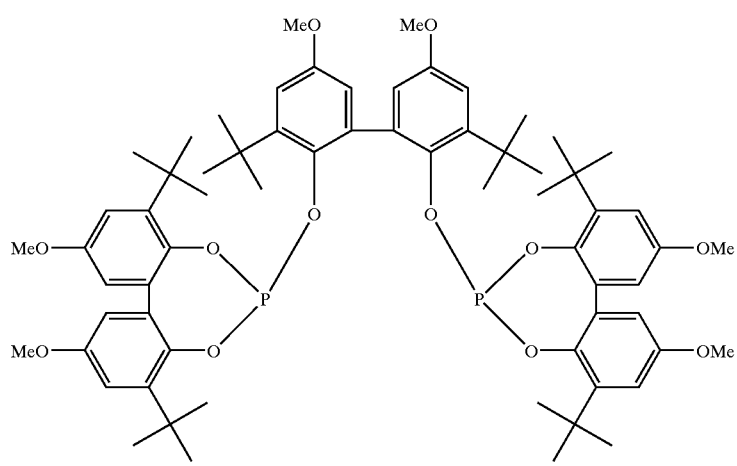
No. 10
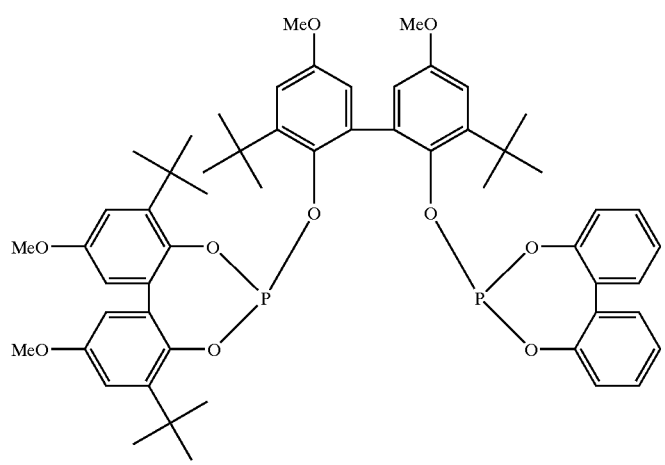

TABLE 2-continued
No. 11
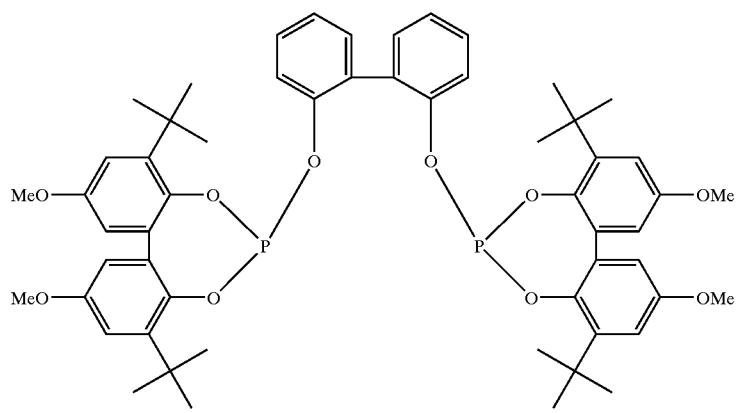
No. 12
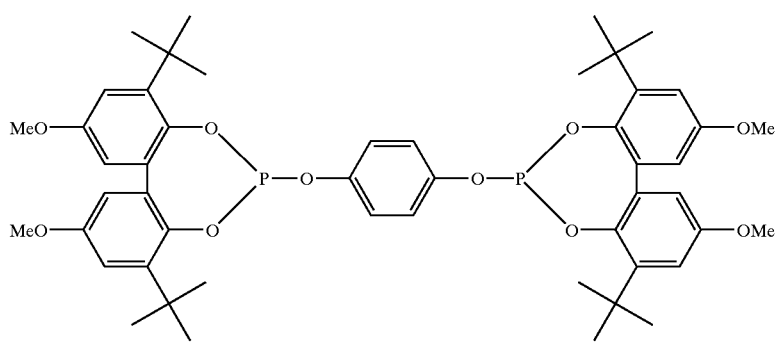
No. 13
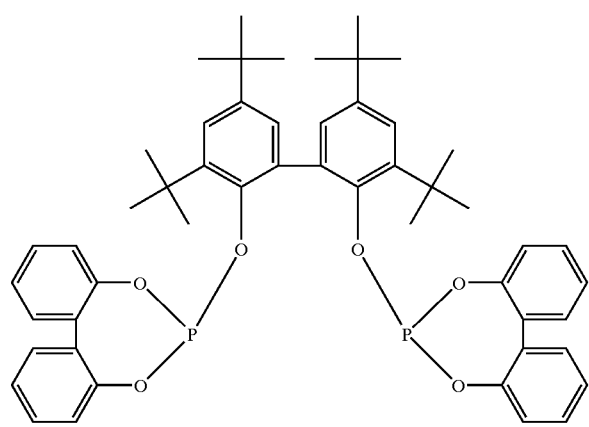
No. 14
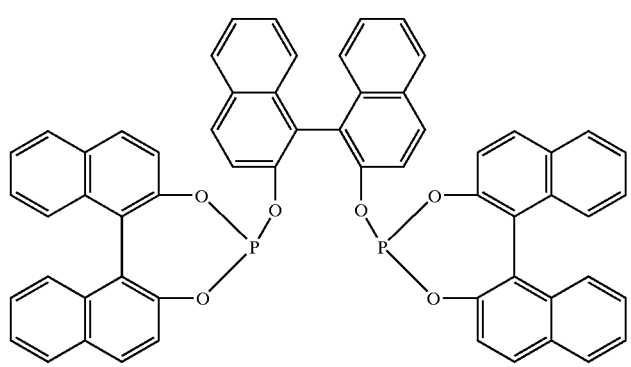

TABLE 2-continued
No. 15
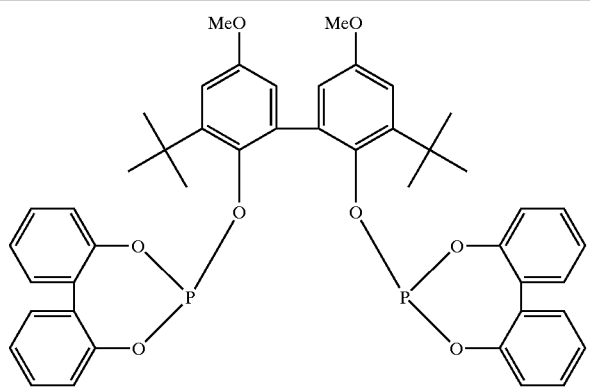
No. 16
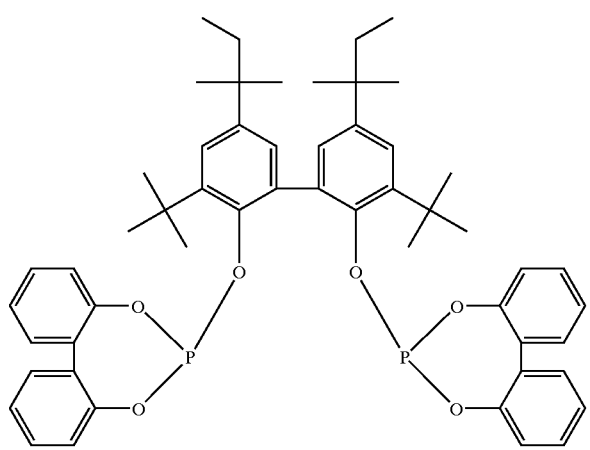
No. 17
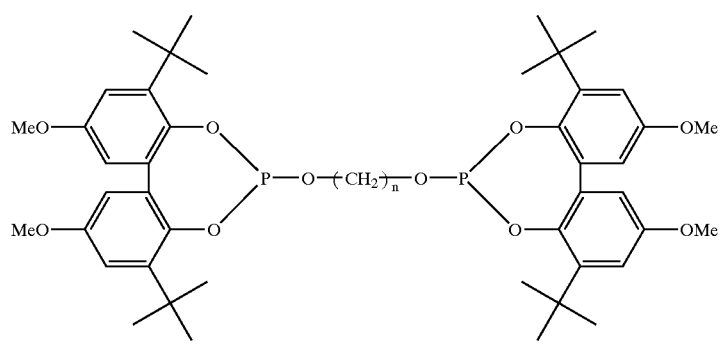
No. 18
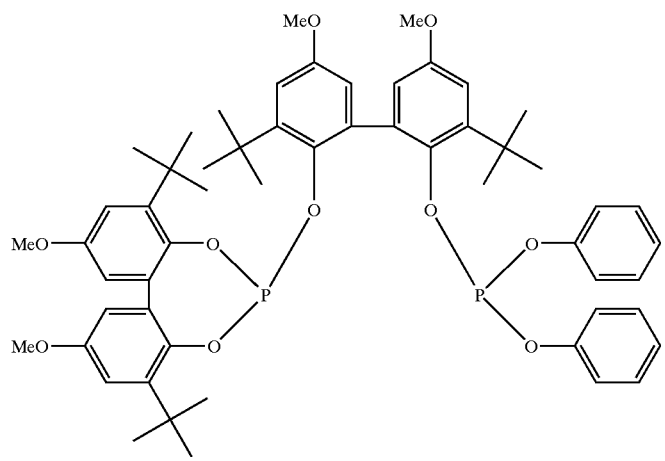

TABLE 2-continued
No. 19
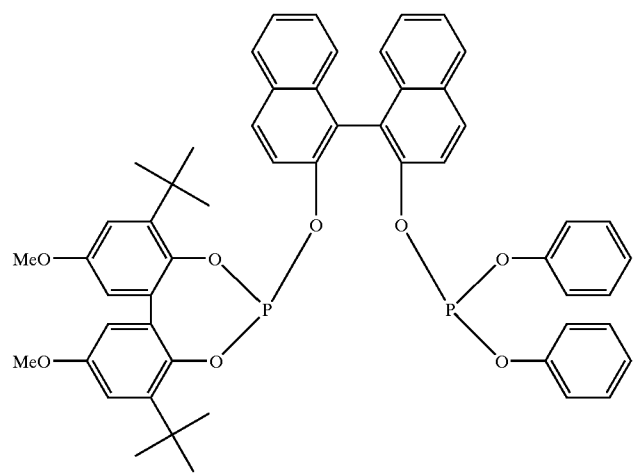
No. 20
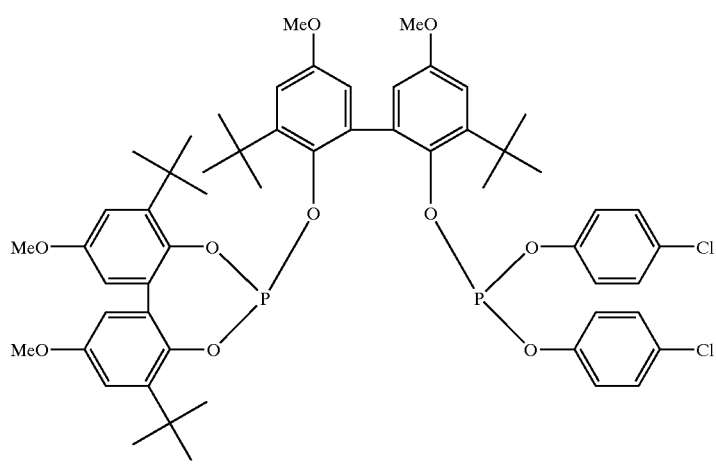
No. 21
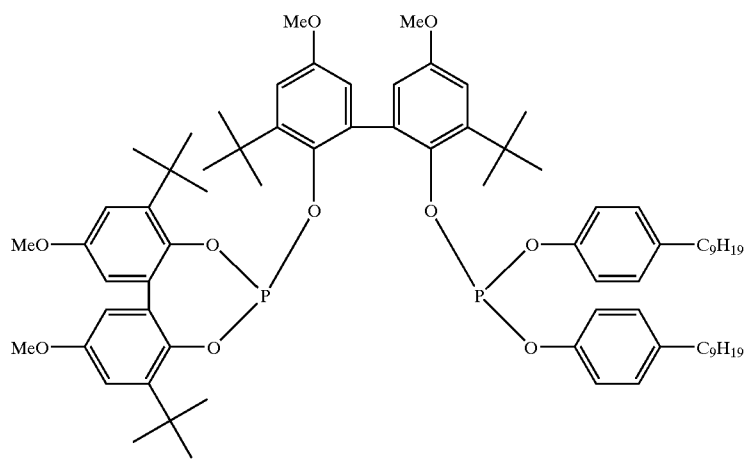

TABLE 2-continued
No. 22
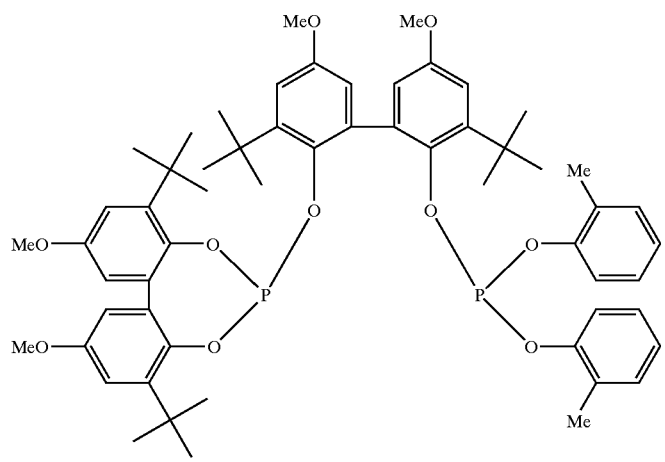
No. 23
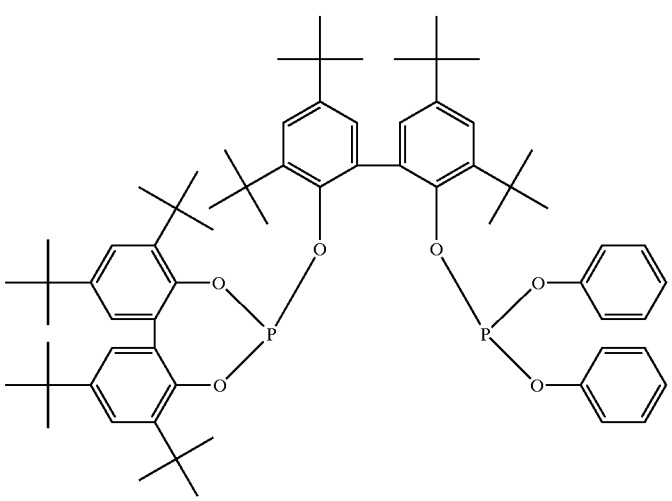
No. 24
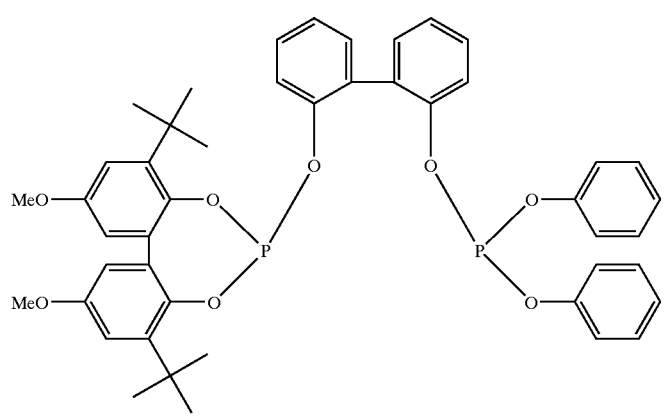

TABLE 2-continued
| No. 25 | 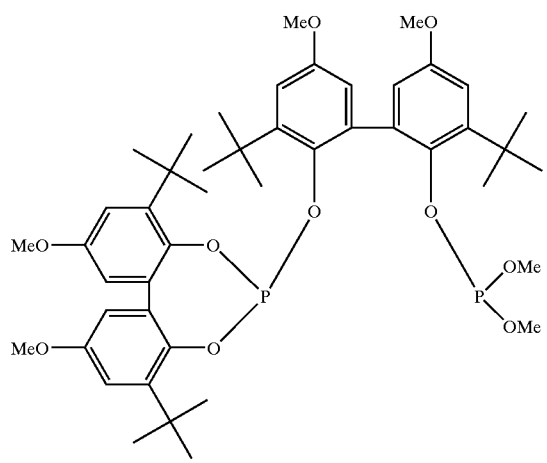 |
| No. 26 | 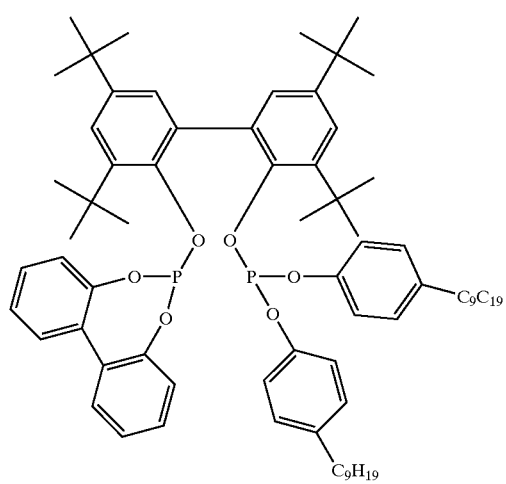 |
| No. 27 | 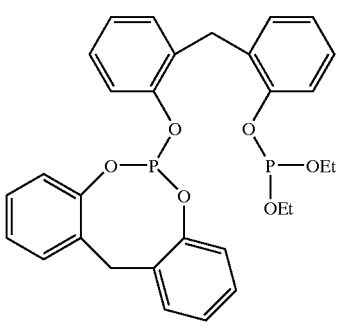 |
| No. 28 | 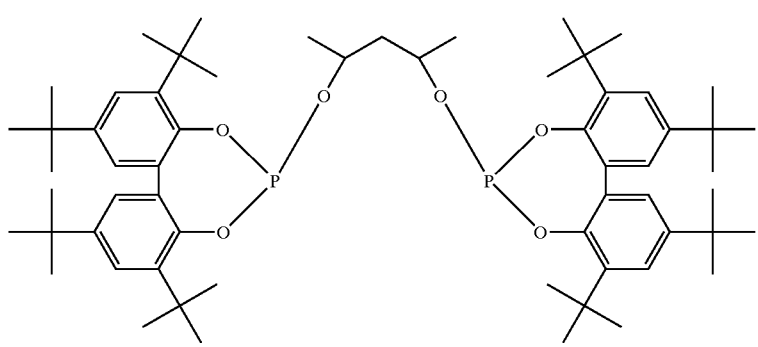 |

TABLE 2-continued
No. 29
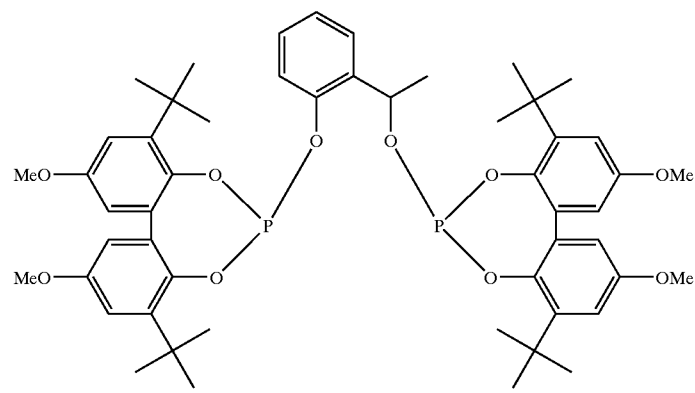
No. 30
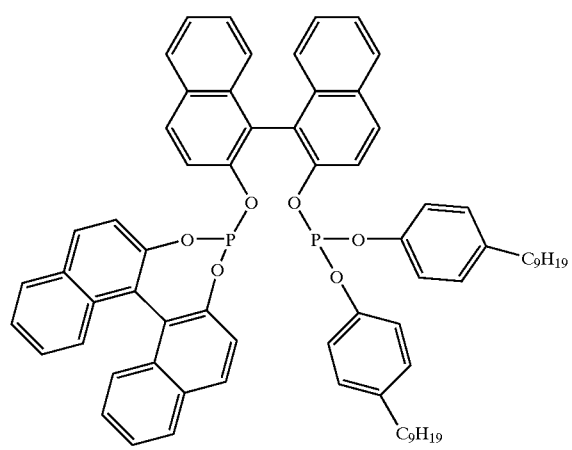
No. 31
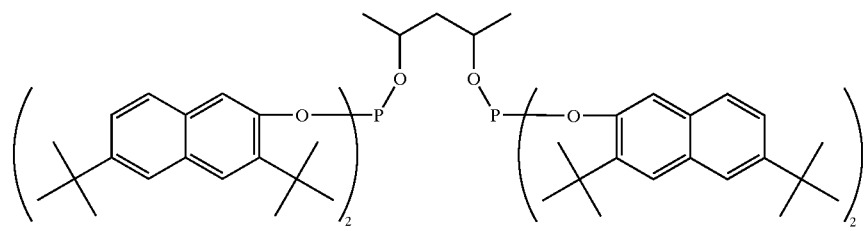
No. 32
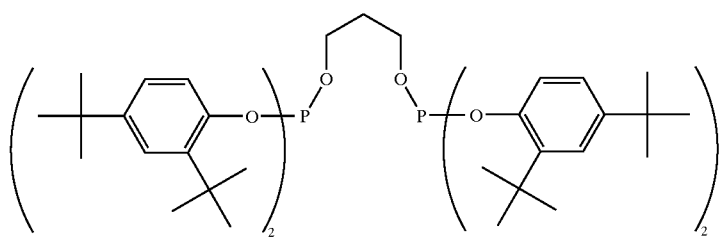
No. 33
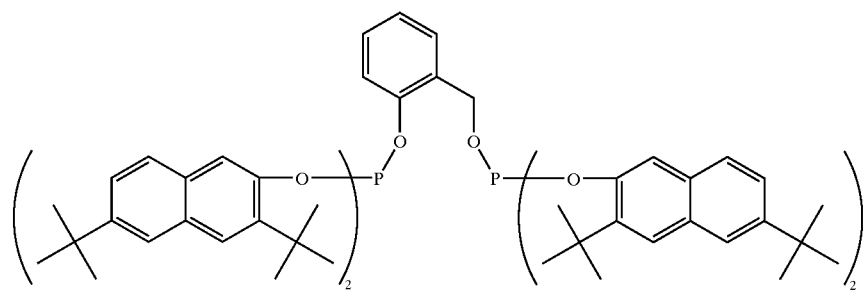

TABLE 2-continued
No. 34
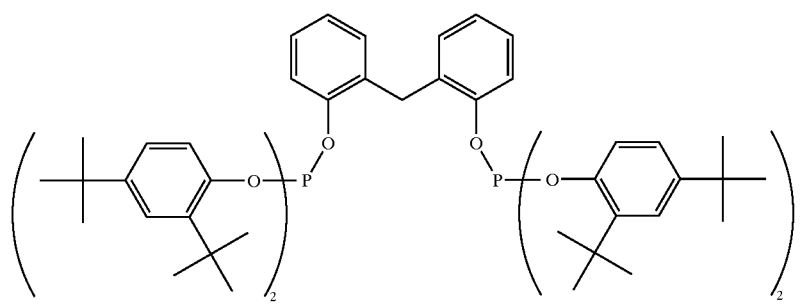
No. 35
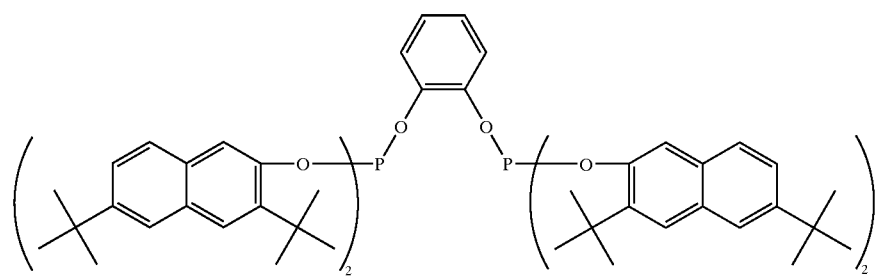
No. 36
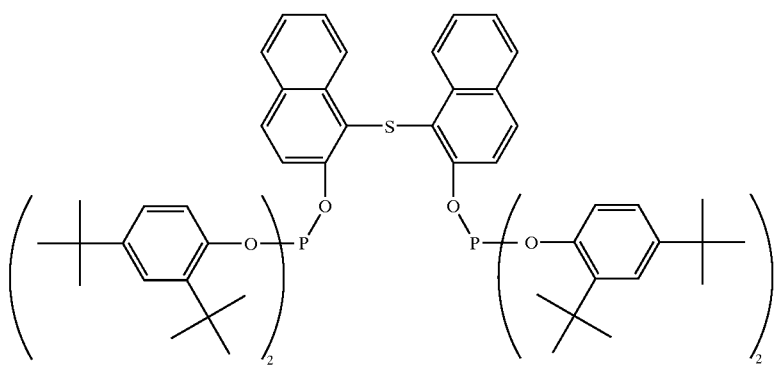
No. 37
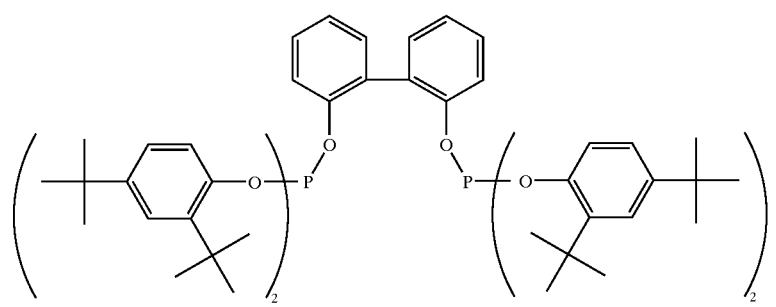

TABLE 2-continued
No. 38
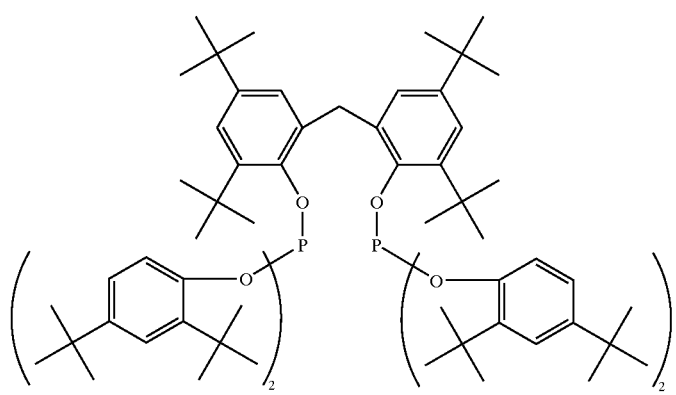
No. 39
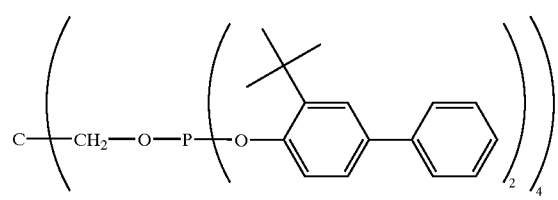
No. 40
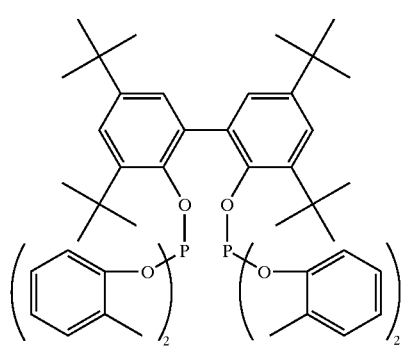
No. 41
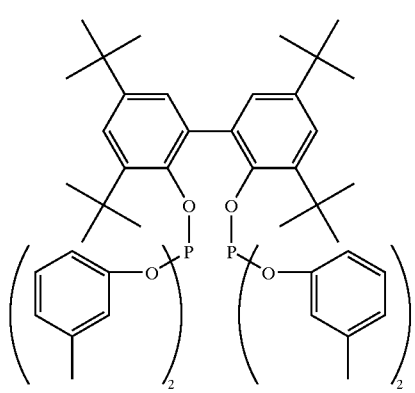

TABLE 2-continued
No. 42
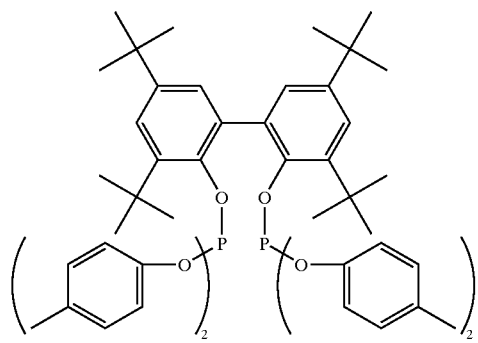
No. 43
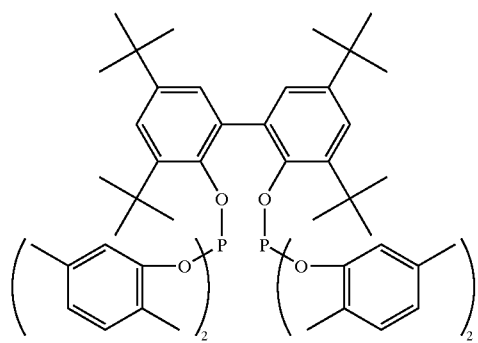
No. 44
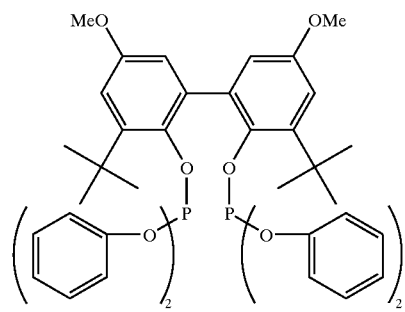
No. 45
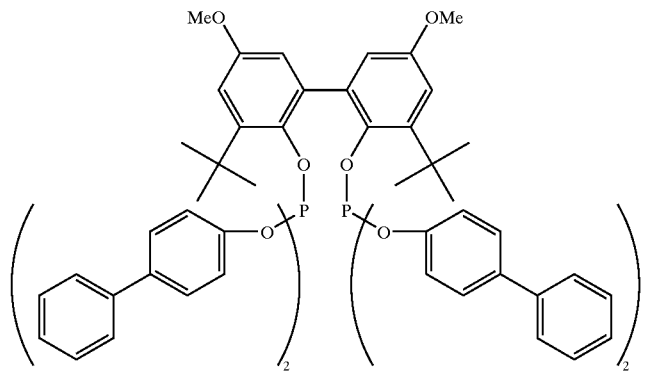

TABLE 2-continued
No. 46
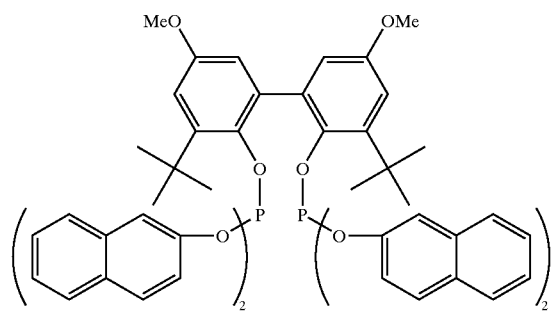
No. 47
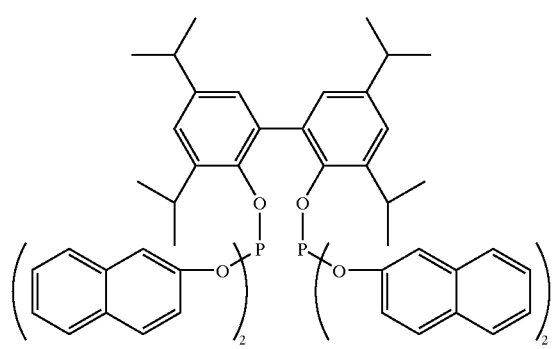
No. 48
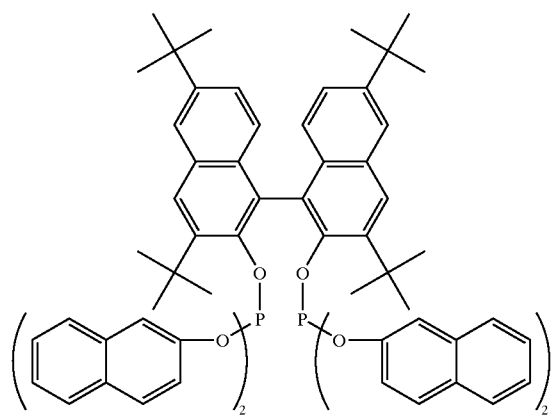
No. 49
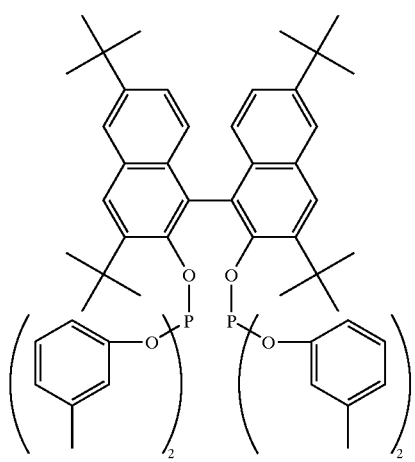

TABLE 2-continued
No. 50
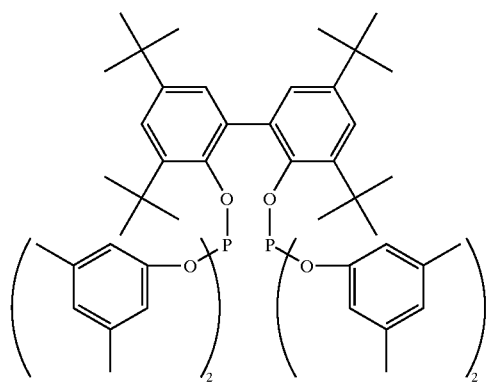
No. 51
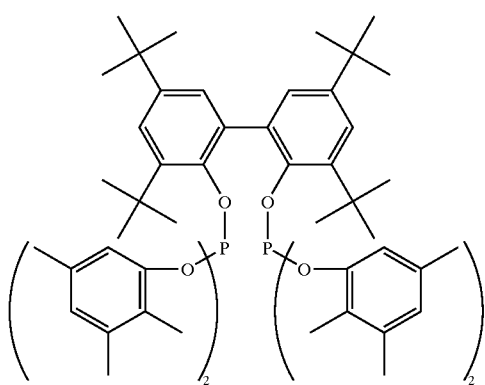
No. 52
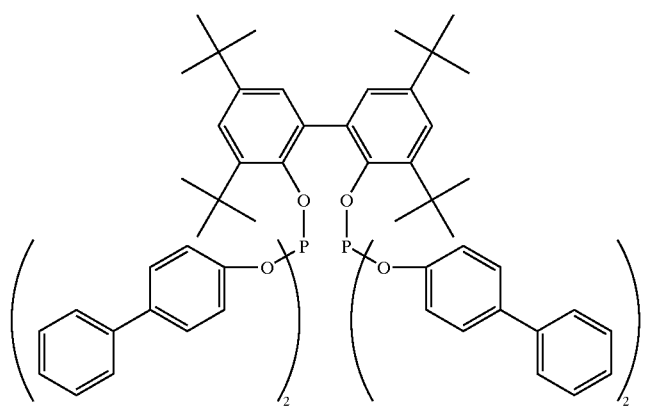
No. 53
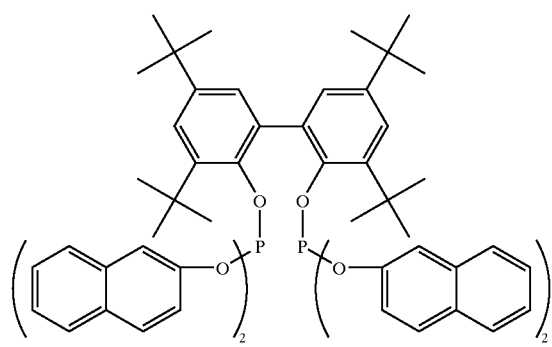

TABLE 2-continued
No. 54
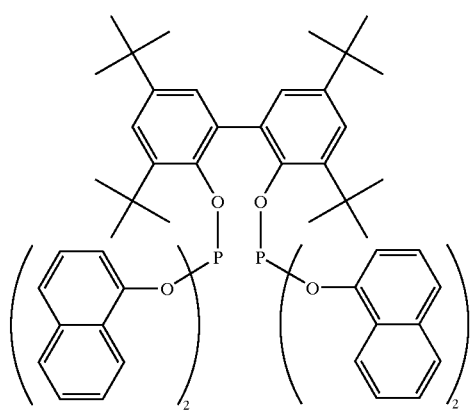
No. 55
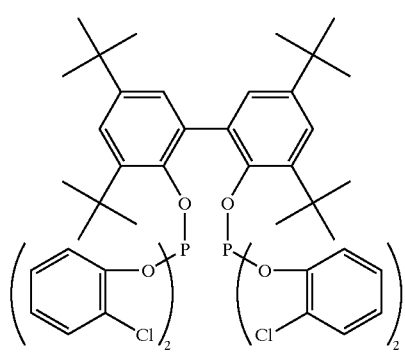
No. 56
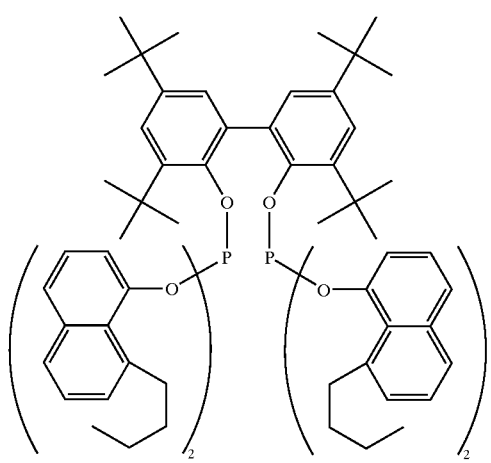
No. 57
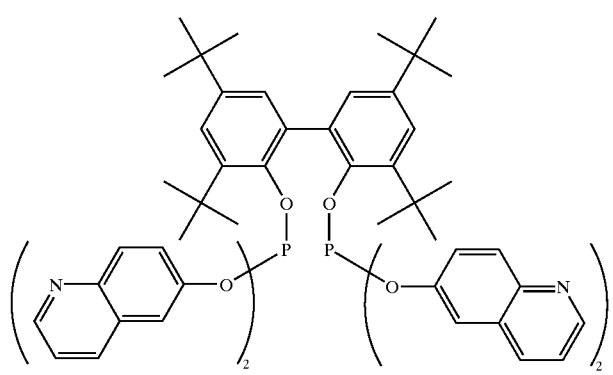

TABLE 2-continued
No. 58
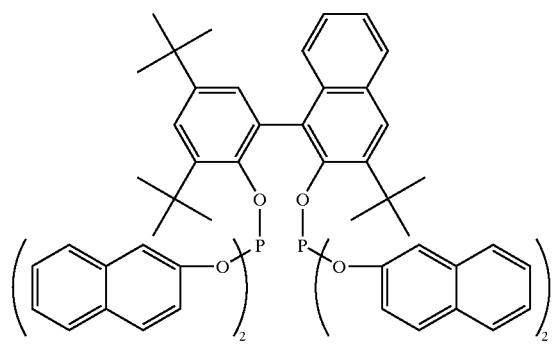
No. 59
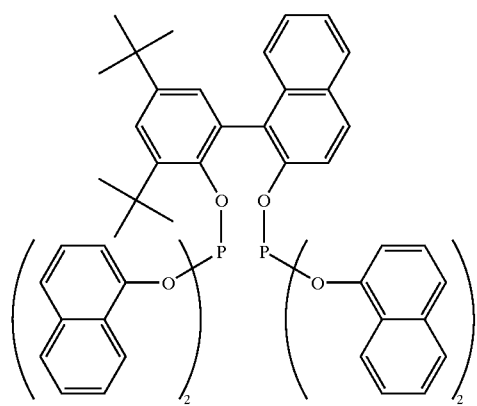
No. 60
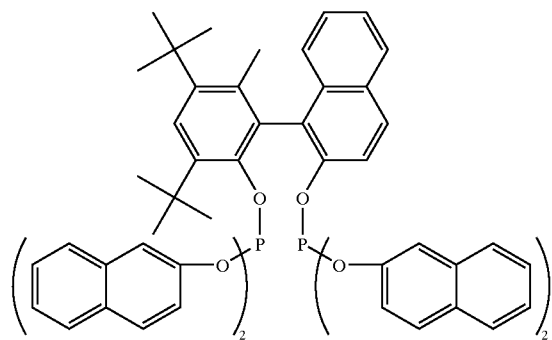
No. 61
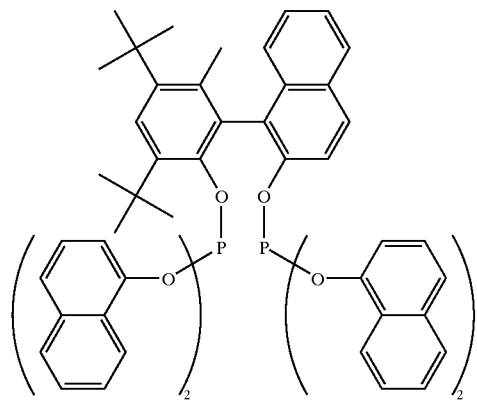

TABLE 2-continued
No. 62
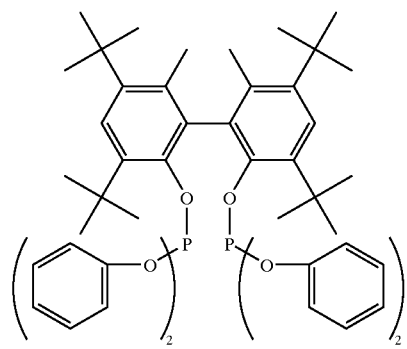
No. 63
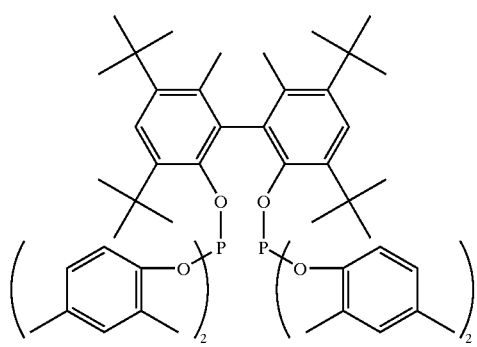
No. 64
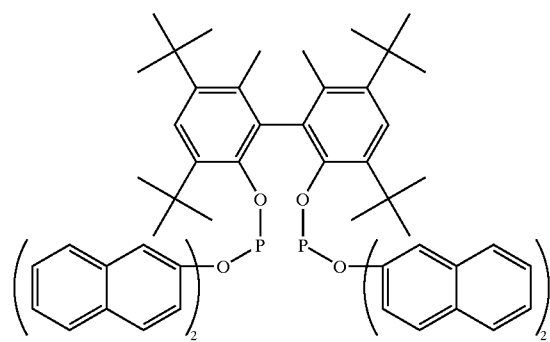
No. 65
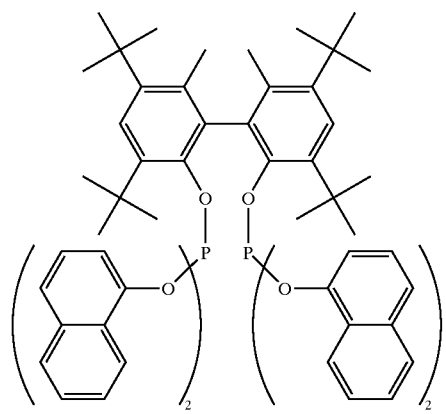

TABLE 2-continued
No. 66
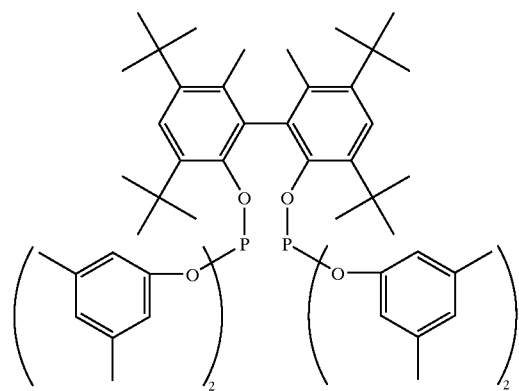
No. 67
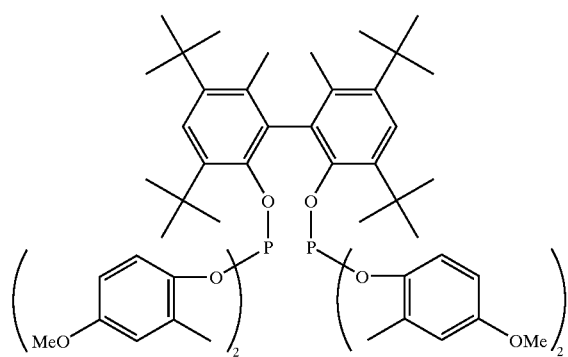
No. 68
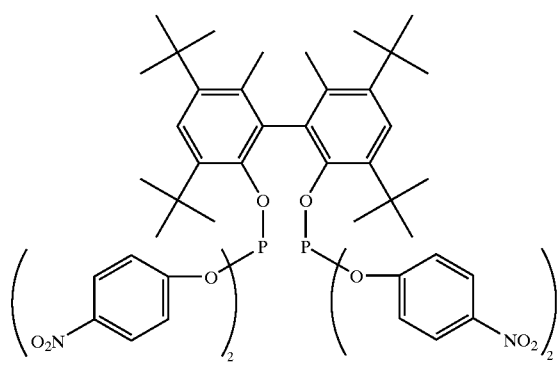
No. 69
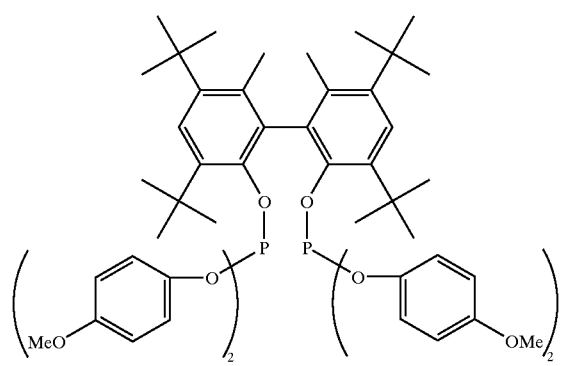

TABLE 2-continued
No. 70
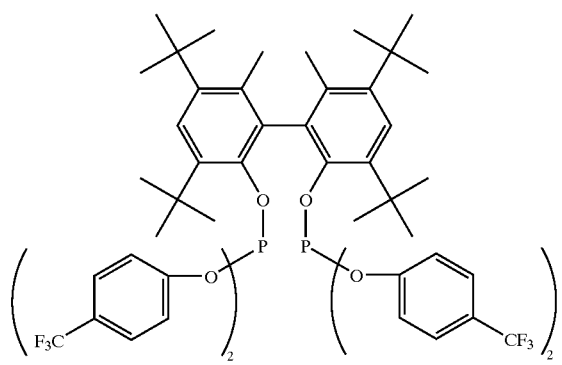
No. 71
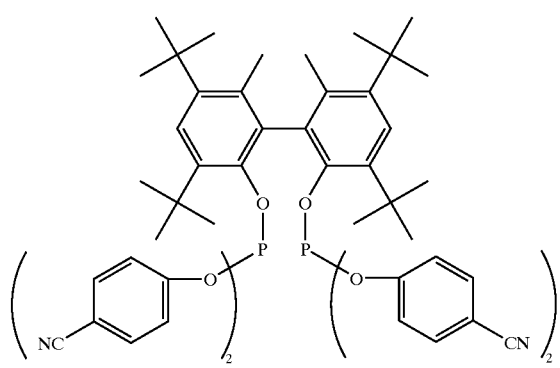
No. 72
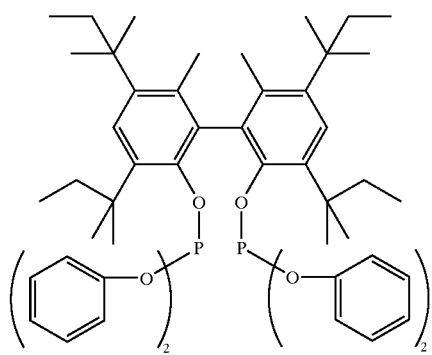
No. 73
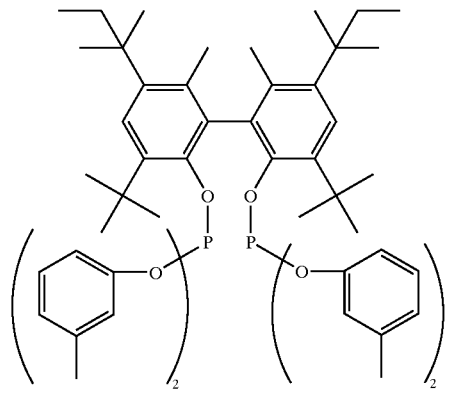

TABLE 2-continued
No. 74
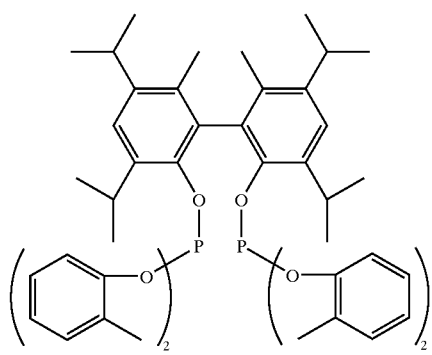
No. 75
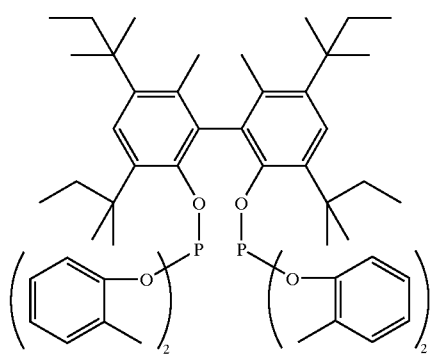
No. 76
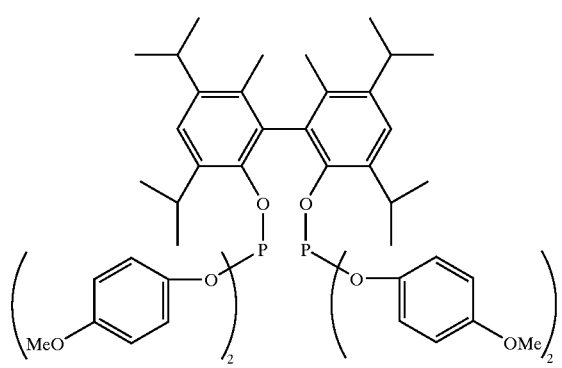
No. 77
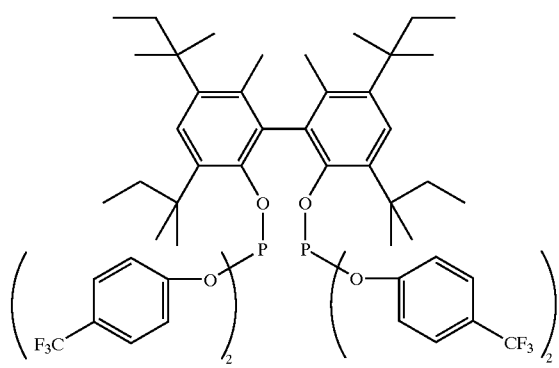

TABLE 2-continued
| No. 78 | 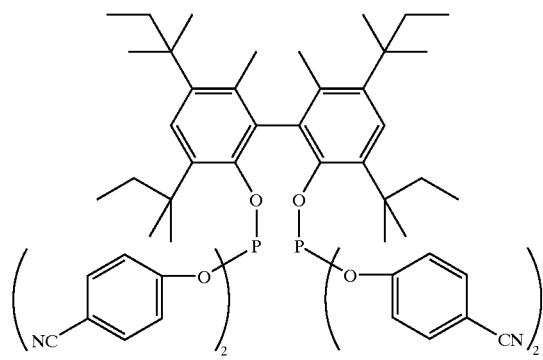 |
| No. 79 | 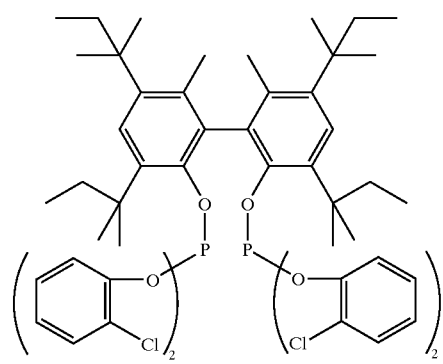 |
| No. 80 | 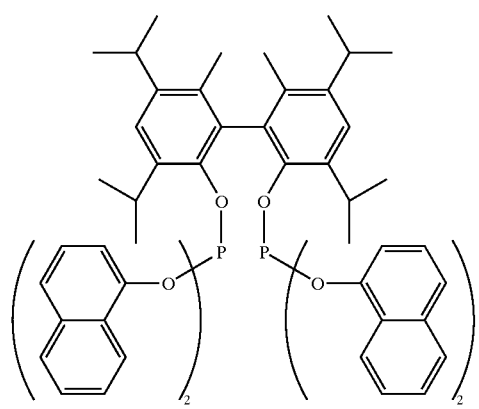 |
| No. 81 | 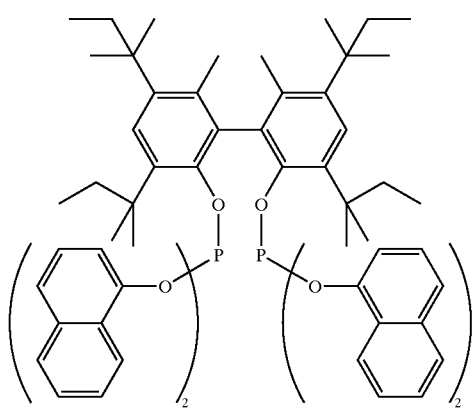 |

TABLE 2-continued
No. 82
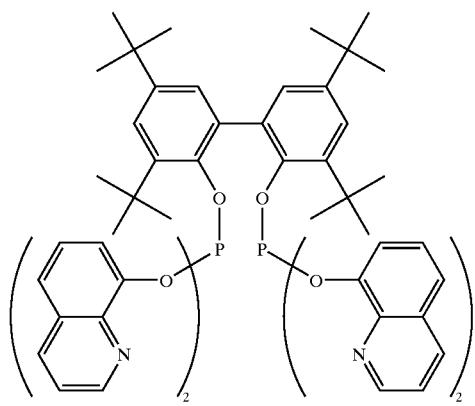
No. 83
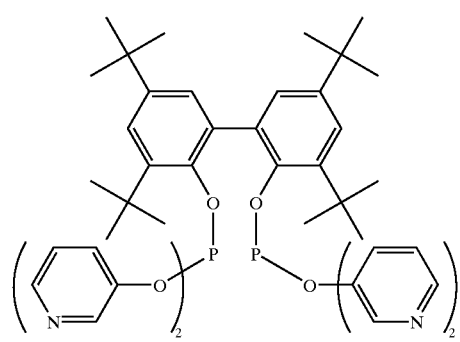
No. 84
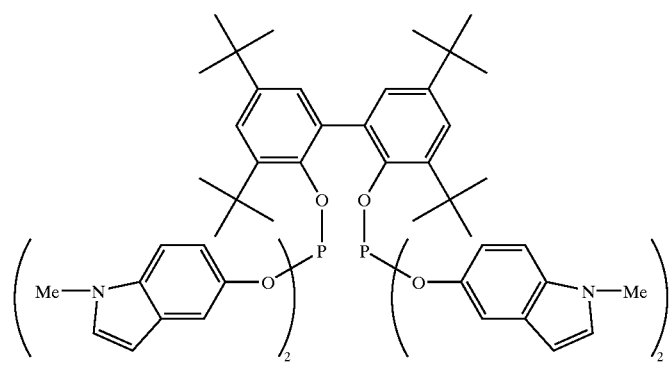
No. 85
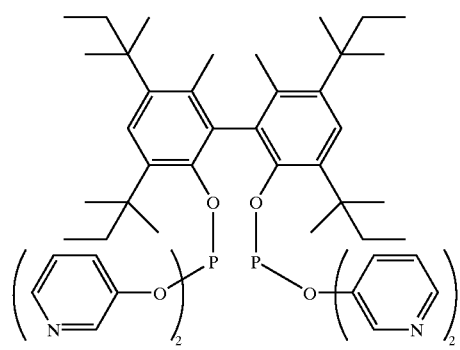

TABLE 2-continued
No. 86
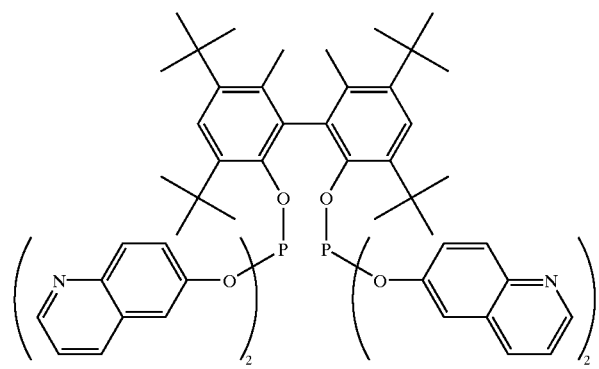
No. 87
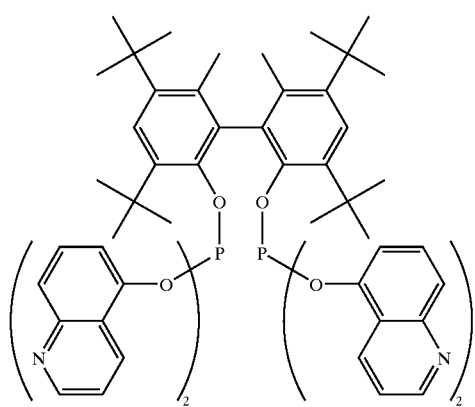
No. 88
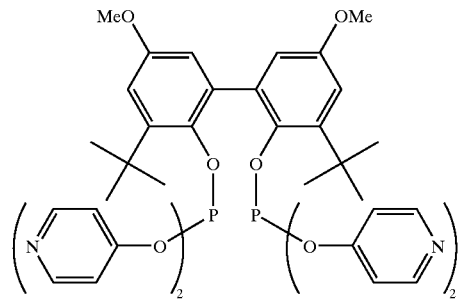
No. 89
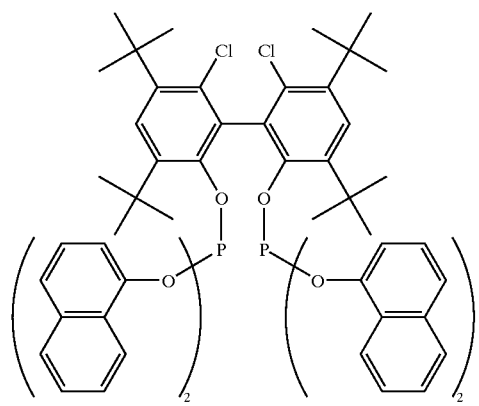

TABLE 2-continued
No. 90
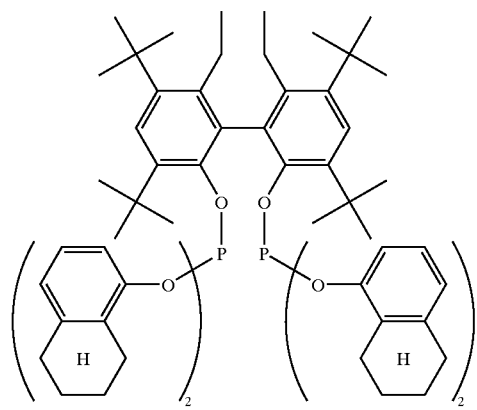
No. 91
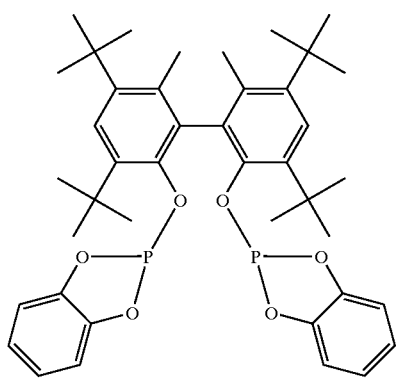
No. 92
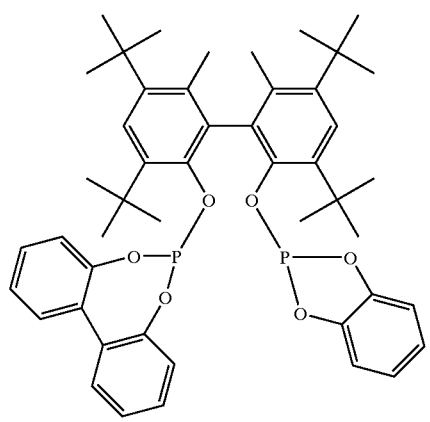

TABLE 2-continued
No. 93
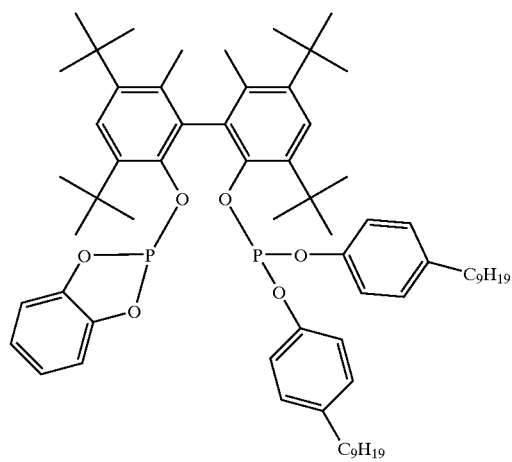
No. 94
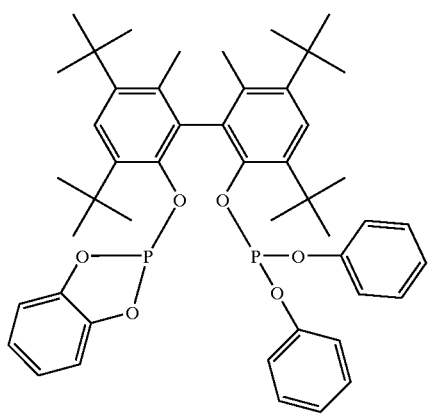
No. 95
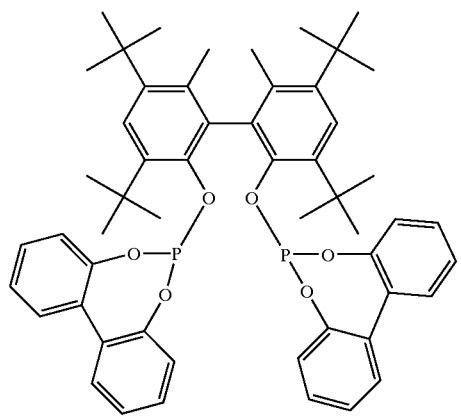

TABLE 2-continued

No. 96

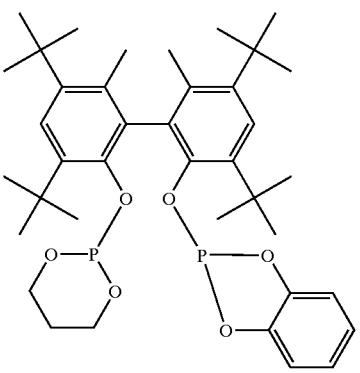

Hydroformylation reaction can be carried out by using an olefinic compound of a starting material as the main solvent, but it is usually preferable to employ a solvent inert to the reaction. Examples of such a solvent include aromatic hydrocarbons such as toluene, xylene, dodecylbenzene or the like, ketones such as acetone, diethylketone, methyl ethyl ketone or the like, ethers such as tetrahydrofuran, dioxane or the like, esters such as ethyl acetate, di-n-octylphthalate or the like, and a mixture of high boiling components by-produced during the hydroformylation reaction, such as an aldehyde condensate, and further an aldehyde per se as a reaction product. Among them, an aromatic hydrocarbon such as toluene, xylene or the like, or a mixture of high boiling components by-produced during the reaction, or a combination thereof, are preferable.

A concentration of a rhodium complex catalyst in a reaction zone is usually from 0.05 to 5,000 mg, preferably from 0.5 to 1,000 mg, more preferably from 10 to 500 mg, as rhodium metal in one litter of liquid phase. An organic phosphite is used in an amount of usually about from 0.1 to 500 time mols, preferably from 0.1 to 100 time mols, more preferably from 1 to 30 time mols, to rhodium. The organic phosphite may be used in a mixture of a few kinds.

Any olefinic compounds may be used as a starting material, provided that they have at least one olefinic double bond in a molecule. The olefinic double bond may be present at the terminal or in the inside of a molecular chain. A carbon chain constituting molecule may be any of linear, branched or cyclic chain. Also, the molecule may contain a carbonyl group, a hydroxyl group, an alkoxy group, an alkoxycarbonyl group, an acyl group, an acyloxy group, a halogen atom or the like, which is substantially inert to hydroformylation reaction. Typical examples of the olefinic unsaturated compound include α-olefin, internal olefin, alkyl alkenoate, alkenyl aklanoate, alkenyl alkylether, alkenol and the like. Some examples of the olefinic unsaturated compound include ethylene, propylene, butene, butadiene, pentene, hexane, hexadiene, octene, octadiene, nonene, decene, hexadecene, octadecene, eicosene, docosene, styrene, α-methylstyrene, cyclohexene, and a lower olefin mixture such as a mixture of propylene/butene, a mixture of 1-butene/2-butene/isobutylene, a mixture of 1-butene/2-butene/isobutylene/butadiene or the like, olefins such as an olefin oligomer isomer mixture of from dimer to tetramer of a lower olefin including propylene, n-butene, isobutylene, and the like, a hydrocarbon olefin such as 3-phenyl-1-propene, 1,4-hexadiene, 1,7-octadiene, 3-cyclohexyl-1-butene, and the like, and polar group-substituted olefins such as acrylonitrile, allyl alcohol, 1-hydroxy-2,7-octadiene, 3-hydroxy-1,7-octadiene, oleyl alcohol, 1-methoxy-2,7-octadiene, methyl acrylate, methyl methacrylate, methyl oleate, oct-1-en-4-ol, vinyl acetate, allyl acetate, 3-butenyl acetate, allyl propionate, vinyl ethyl ether, vinyl methyl ether, allyl ethyl ether, n-propyl-7-octenoate, 3-butenenitrile, 5-hexenamide and the like. Preferably, a monoolefinic unsaturated compound having only one olefinic double bond in a molecule is used. More preferably, a $C_2$–$C_{20}$ olefin such as propylene, 1-butene, 2-butene, isobutene, and their mixture, 1-octene, mixed octene, and the like.

The reaction temperature of hydroformylation reaction is usually in the range of from 15 to 150° C., preferably from 30 to 130° C., more preferably from 50 to 110° C. The reaction pressure is usually in the range of from normal pressure to 200 kg/cm$^2$G, preferably from 1 to 100 kg/cm$^2$G, most preferably from 3 to 50 kg/cm$^2$G. A molar ratio of hydrogen of oxo gas/carbon monoxide ($H_2$/CO) to be charged into the reaction zone is usually in the range of from 10/1 to 1/10, preferably from 1/1 to 6/1.

The reaction can be carried out by any system of continuous system and batchwise system, but is usually carried out by continuous system. Thus, a reaction solvent containing a catalyst, a starting olefinic compound and oxo gas are continuously charged into the reaction zone, and a reaction product solution containing an aldehyde product is continuously withdrawn from the reaction zone, and a reaction solvent containing a catalyst remaining after separating at least the aldehyde product is continuously recycled into the reaction zone as a catalyst solution. The separation of the aldehyde product can be carried out by optional method, but is usually carried out by distillation. When the separation of aldehyde from the reaction product solution is carried out by distillation, a rhodium complex catalyst is generally easily deactivated. Particularly, since a rhodium complex catalyst of the present invention having an organic phosphite as a ligand has a high activity, the hydroformylation reaction is often carried out at such a relatively low temperature as mentioned above, and the distillation temperature of separating aldehyde from the reaction product solution becomes higher, and in such a case, the deactivation of the rhodium complex catalyst is mainly caused in this distillation step.

Accordingly, the distillation is carried out preferably at a temperature of at most 150° C., more preferably at most 130° C., most preferably from 50 to 120° C. When the boiling point of an aldehyde product is high, it is preferable to employ vacuum distillation usually under a reduced pressure in the range of from 755 mmHg to 1 mmHg, preferably from 750 mmHg to 5 mmHg.

One of main causes of the deactivation of the rhodium complex catalyst during distillation is due to the fact that the rhodium complex becomes an unsaturated coordination state since carbon monoxide and hydrogen easily coordinatable to rhodium are not present in the distillation system, and it is considered that an organic phosphonate of the formula (a) formed from an organic phosphite is bonded to the rhodium complex, thereby deactivating the catalyst activity of rhodium.

$$HP(O)(OX^1)(OX^2) \tag{a}$$

(Wherein $X^1$ is hydrogen or a monovalent organic group, and $X^2$ is a monovalent organic group, and $X^1$ and $X^2$ may be bonded to each other to form a divalent organic group.)

Details of the mechanism are not clear, but it is considered that P—H bond of the organic phosphonate is oxidatively added to rhodium metal, or phosphorous acid diester, i.e. a trivalent phosphorus compound present as a tautomerism isomer of an organic phosphonate, is coordinated to rhodium metal.

The tendency that an organic phosphonate poisons the rhodium complex catalyst varies depending on the organic phosphonate structure, and an organic phosphonate having a large steric hindrance generally has a less poisoning function. It is therefore considered that an organic phosphonate having a substituent on a carbon atom adjacent to a carbon atom having an oxygen atom bonded to a phosphorus atom, for example, in the organic phosphonate of the formula (11) formed from the organic phosphite of the formula (3) or the organic phosphonate of the formula (12) formed from the organic phosphite of the formula (9), has a less poisoning function.

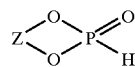
(11)

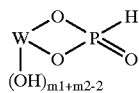
(12)

It is considered that the mechanism of forming an organic phosphonate from an organic phosphite is hydrolysis. Thus, when one of substituents of the organic phosphite is lost by hydrolysis, phosphorous acid diester is formed, which is converted to an organic phosphonate by tautomerism. Accordingly, the organic phosphite of the formula (3) produces the organic phosphonate of the formula (11). The organic phosphonate of the formula (12) is not produced by simple hydrolysis of the organic phosphite of the formula (9), but is produced by way of splitting and rebonding of P—O bond. The organic phosphite of the formula (9) produces the following organic phosphonates in addition to the organic phosphonate of the formula (12).

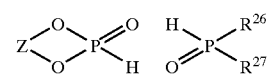

Also, the organic phosphite of the formula (9) produces the following organic phosphonates.

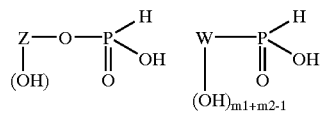

Some examples of the organic phosphonate which are considered to be produced from the organic phosphites of Table 2 are illustrated in the following Table 3.

TABLE 3

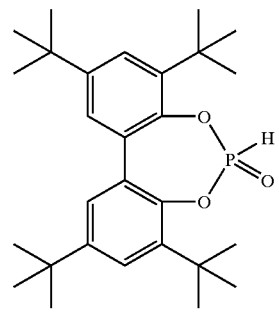 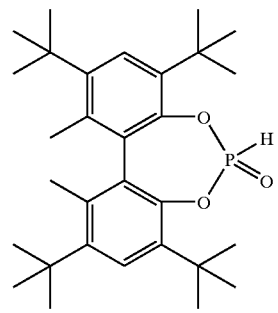 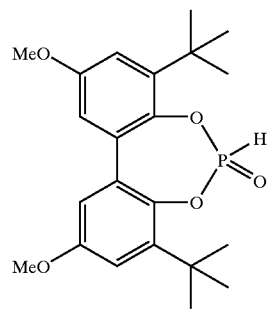

No. 1　　　　　　　No. 2　　　　　　　No. 3

TABLE 3-continued
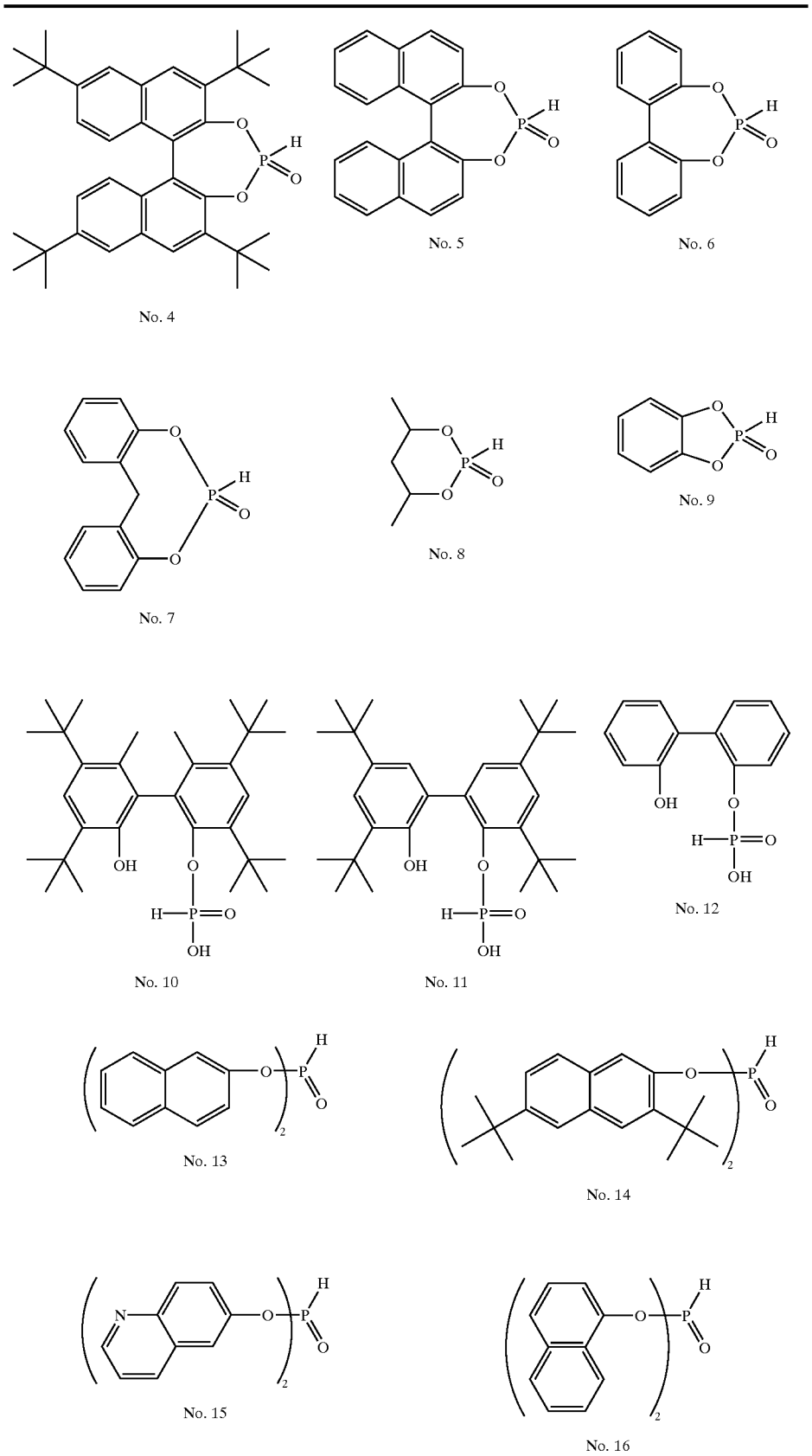

TABLE 3-continued

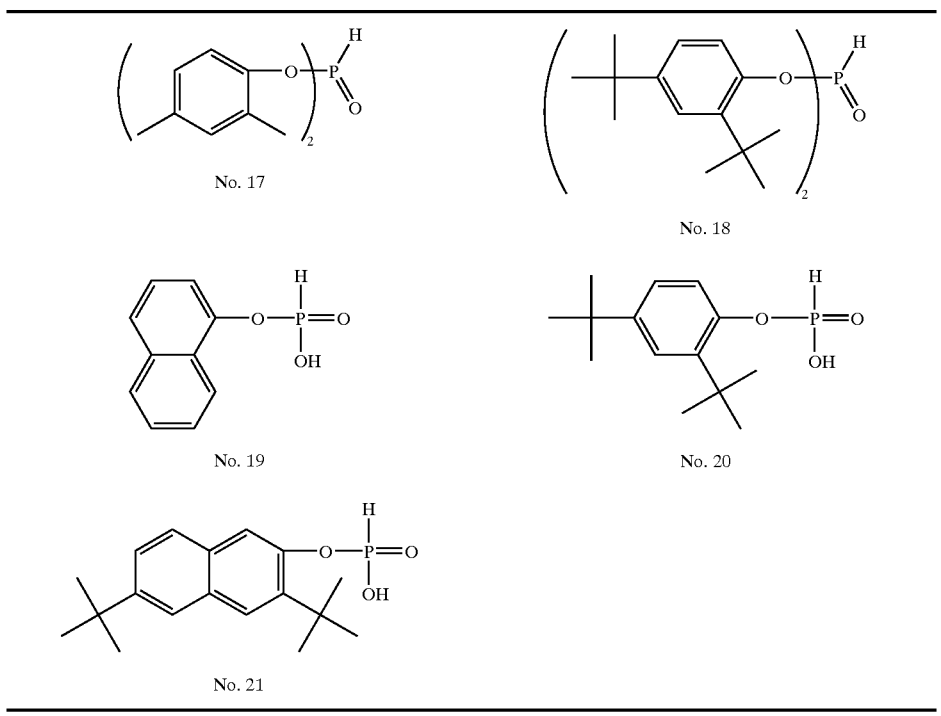

In the present invention, when recovering a catalyst solution, i.e. a solution containing a rhodium complex catalyst, from a reaction product solution in the separation step, an aldehyde is made present in the catalyst solution. The aldehyde reacts with an organic phosphonate to form a hydroxyalkylphosphonic acid, which is less poisonous to the rhodium catalyst as compared with the organic phosphonate. The reason is not clear, but since the hydroxyalkylphosphonic acid can not be a trivalent structure by tautomerism and does not have a P—H bond to be oxidatively added to rhodium metal, the hydroxyalkylsulfonic acid basically can not bond with rhodium and is therefore less poisonous.

An aldehyde is made present in an amount of at least equivalent mol to an organic phosphonate in a catalyst solution, but is usually made present in an amount of from 0.5 to 99 wt %. The term "catalyst solution" means a solution containing a solvent and a catalyst after separating a reaction product from a reaction product solution. In order to remove an organic phosphonate by accelerating reaction between the organic phosphonate and the aldehyde, it is preferable to make an aldehyde concentration in the catalyst solution higher, for example, at least 1 wt %, more preferably at least 3 wt % in the catalyst solution. Also, when the produced aldehyde is used as a reaction solvent, the aldehyde concentration in the catalyst solution may be high, but in such a case, an amount of the aldehyde charged into the reaction zone increases, and causes a side-reaction such as aldol condensation. Therefore, it is preferable to make the aldehyde concentration in the catalyst solution at most 70 wt %, more preferably at most 50 wt %, most preferably at most 25 wt %.

As mentioned above, an organic phosphonate lowers a catalyst activity, and becomes an intermediate of a component for accelerating decomposition of an organic phosphite, and therefore it is not preferable to make the organic phosphonate present in a large amount. On the other hand, if the amount of the organic phosphonate is small, the stability of rhodium is unexpectedly improved. This stabilizing effect becomes more effective when an amount of coexisting organic phosphite is decreased, e.g. when P/Ph ratio in the organic phosphite is 0.1–10, preferably 0.5–5. Thus, in the hydroformylation reaction of using a complex catalyst comprising rhodium and an organic phosphite, there is a case where an insoluble rhodium compound is formed in a minor amount. The structure of the insoluble rhodium compound is not clear, but it is considered that it is formed by way of a rhodium material not stabilized by the organic phosphite or other ligand. Thus, it is considered that the organic phosphonate is coordinated also to the coordination-unsaturated rhodium material, and consequently the stability is improved. That is, if the amount of the organic phosphonate is controlled in a predetermined range, a catalyst is not poisoned but rather stabilized. Accordingly, depending on the structure of the organic phosphonate, the stabilizing effect of rhodium becomes high or the poisoning effect of catalyst becomes high even when its presence is minor.

Thus, the amount of the organic phosphonate to coexist with rhodium varies depending on the structure of the organic phosphonate, but is usually from 0.0001 to 5 time mols, preferably from 0.001 to 3 time mols, most preferably from 0.01 to 1.5 time mols, to rhodium metal. Among them, the amount in the range of from 0.05 to 1 time mol is particularly most preferable. Also, the range of a preferable amount varies depending on the structure of the organic phosphonate. Generally, an organic phosphonate, the steric hindrance of which is not large, is largely poisonous, and the organic phosphonates of the formulae (1) and (13) and the organic phosphonates having no substituent on a carbon atom adjacent to a carbon atom having an oxygen atom bonded to a phosphorus atom in Z of the formula (15) and in W of the formula (12) are largely poisonous. Such organic phosphonates are present preferably in an amount of from 0.001 to 2 time mols, more preferably from 0.001 to 1 time mol, to rhodium metal. In the present specification, an amount of an organic phosphonate includes not only an organic phosphonate present in a free state but also an organic phosphonate forming a complex by bonding to rhodium metal. Thus, the amount of the organic phosphonate is a total amount of that of free state and that of bonded state.

An organic phosphonate can be quantitatively measured generally by high speed liquid chromatography, NMR spectrum or the like.

According to one preferable embodiment of the present invention, an olefinic compound, mixture of hydrogen and carbon monoxide gas and a catalyst solution are continuously charged into a stirring tank type reactor or a bubbling column type reactor to produce an aldehyde. A reaction product solution is continuously withdrawn from the reactor as a gas-liquid mixture phase current, and is introduced into a gas-liquid separator wherein a gas phase comprising unreacted hydrogen and carbon monoxide gas and sometimes unreacted olefinic compound and a liquid phase comprising the reaction product solution are separated. The gas phase is pressurized and is recycled into the reactor. In the recycling step, it is preferable to remove a part of the gas outside the system in order to prevent accumulation of impurities. The liquid phase is distilled in a distillation column, and an aldehyde is distilled out from the top of the distillation column, and a rhodium complex catalyst and a catalyst solution containing an aldehyde at a predetermined concentration are recovered from the bottom of the distillation column and are recycled into the reactor. In the recycling step, in order to prevent accumulation of an aldol condensation product, it is preferable to remove a part of the catalyst solution out of the system and to purify the catalyst solution by extraction, crystallization or other means. The rhodium and organic phosphite thus lost by these operations are freshly supplied, and the amount of rhodium and an organic phosphite in the system are maintained substantially constant.

According to the present invention, it is possible to carry out the reaction for a long period of time, usually at least 1 month, without refreshing a catalyst. From economical viewpoint, it is preferable to use the catalyst as long as possible, and according to the present invention, it is possible to continuously use the catalyst for a long period of time of at least 6 months, if desired, at least 1 year.

Aldehydes obtained by the process of the present invention can be used as they are, for hydrogenation reaction in accordance with well known methods including the methods disclosed in U.S. Pat. Nos. 5,550,302 and 5,657,644, or for hydrogenation reaction after dimerization, to produce an alcohol such as n-butanol, 2-ethyl hexanol, nonyl alcohol and the like, suitable as a plasticizer.

EXAMPLES

Hereinafter, the present invention is further illustrated with reference to Examples, but should not be limited thereto.

Reference Example 1

Preparation of Phosphonate (I)

About 250 ml of a toluene solution having 12.37 g (28.2 mmol) of 3,3',5,5'-tetra-t-butyl-6,6'-dimethyl-2,2'-hydroxybiphenyl and 9.62 g (95.1 mmol) of triethylamine dissolved was dropwise added to about 300 ml of a toluene solution having 4.22 g (30.7 mmol) of phosphorus trichloride dissolved, under stirring in an nitrogen atmosphere at 0° C. for 1.5 hours. Thereafter, the resultant mixture was heated to 70° C., and was stirred for 1 hour, and was then cooled to room temperature, and was filtrated to remove triethylamine hydrochloride salt precipitated. 100 ml of water was added to the filtrate, and the resultant mixture was heated to 70° C. and was stirred for 1 hour. A toluene phase was taken by separation, and was washed with water 3 times, and was washed with saturated brine 3 times. The toluene phase thus treated was dehydrated by anhydrous magnesium sulfate, and the solvent was distilled off. To the residue thus obtained, were added a small amount of toluene and about 50 ml of acetonitrile, and the resultant mixture was stirred in suspension state, and was then filtrated. A solid obtained was dried under reduced pressure and 7.15 g (yield 52%) of 0,0'-3,3',5,5'-tetra-t-butyl-6,6'-dimethyl-2,2'-diylphosphonate of the following formula was obtained. This product is referred to as "phosphonate (I)".

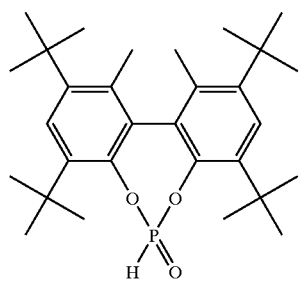

Reference Example 2

Preparation of Rhodium-phosphonate Complex

The above complex was prepared in accordance with Faraone method disclosed in J. Chem. Soc., Dalton Trans. 4357 (1996).

532.5 mg (2.06 mmol) of rhodium dicarbonyl acetyl acetonate complex and 2.00 g (4.13 mmol) of phosphonate (I) were dissolved in 250 ml of dry toluene. The resultant solution was stirred in a nitrogen atmosphere at room temperature for 25 hours, and the toluene was distilled off under reduced pressure. The residue thus obtained was dissolved in 100 ml of hexane, and was filtrated to remove insoluble materials, and the filtrate was distilled under reduced pressure, and to the residue thus obtained, was added acetonitrile, and the resultant mixture was stirred in suspension state. The mixture was then filtrated to obtain a yellow powdery solid. The product is considered to have the following structure.

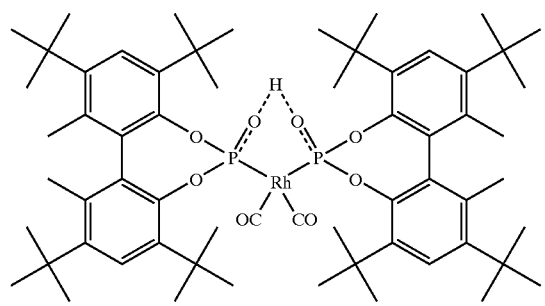

According to $^{31}$P-NMR analysis, the main product has a purity of 82%, and there was formed other phosphonate complex, the structure of which was not clear. The main product had the following spectrum data.

$^{31}$P-NMR (162 MHz, CDCl$_3$); δ111.2d, J=197 Hz $^1$H-NMR (400 MHz, CDCl$_3$, 23° C.); δ1.39 (18H,s), 1.40(18H,s), 1.44(18H,s), 1.51(18H,s), 1.94(6H,s), 2.03(6H,s), 7.40(2H,s), 7.42(2H,s)

IR(CDCl$_3$) 2098, 2057 cm$^{-1}$

Example 1

Into a stainless-made autoclave having an internal volume of 100 ml, were charged 273.8 mg of the above prepared rhodium-phosphonate complex, 1.0408 g of the following organic phosphite, 25 ml of toluene and 25ml of n-butyraldehyde in a nitrogen atmosphere. During the charge, rhodium concentration was 500 mg/l, mol ratio of organic phosphite to rhodium was 4, mol ratio of organic phosphonate to rhodium was 2, and aldehyde concentration was 48 wt %. The autoclave was sealed, and the content was heated to 90° C. while stirring. $^{31}$P-NMR analysis data of the reaction solution after maintaining at this temperature for a predetermined time are shown in the following Table. According to $^{31}$P-NMR, phosphonate complex, phosphonate and phosphonic acid exhibit signals respectively at different chemical shift, and they can be quantitatively determined by their integrals.

| Reaction time | 1 | 12 |
|---|---|---|
| Remaining ratio of rhodium-phosphonate complex (%) | 77 | 0 |
| Production ratio of organic phosphonate (I) (%) | 16 | 21 |
| Production ratio of hydroxybutylphosphonic acid (%) | 8 | 79 |

Organic phosphate:

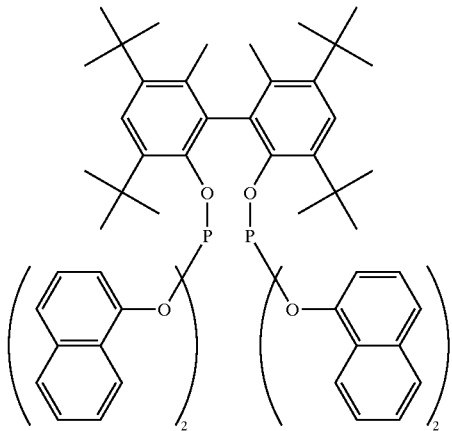

Example 2

The same procedure as in Example 1 was repeated, except that toluene was charged in an amount of 49.5 ml and n-butyraldehyde was charged in an amount of 0.56 ml. The aldehyde concentration in the charged solution was 1 wt %. The results are shown in the following Table.

| Reaction time | 1 | 12 |
|---|---|---|
| Remaining ratio of rhodium-phosphonate complex (%) | 84 | 5 |
| Production ratio of organic phosphonate (I) (%) | 12 | 67 |
| Production ratio of hydroxybutylphosphonic acid (%) | 4 | 28 |

Comparative Example 1

The same procedure as in Example 1 was repeated, except that the nitrogen gas was replaced by oxo gas (mixed gas of hydrogen: carbon monoxide=1:1 (mol ratio)) and the reaction mixture was maintained under a pressure of 5 kg/cm$^2$G at 90° C. The results are shown in the following Table.

| Reaction time | 1 | 4 |
|---|---|---|
| Remaining ratio of rhodium-phosphonate complex (%) | 20 | 0 |
| Production ratio of organic phosphonate (I) (%) | 72 | 34 |
| Production ratio of hydroxybutylphosphonic acid | 9 | 66 |

Comparative Example 2

The same procedure as in Example 1 was repeated, except that toluene was charged in an amount of 50 ml and n-butyraldehyde was not charged. The results are shown in the following Table.

| Reaction time | 1 | 12 | 24 |
|---|---|---|---|
| Remaining ratio of rhodium-phosphonate complex (%) | 98 | 46 | 8 |
| Production ratio of organic phosphonate (I) (%) | 3 | 54 | 92 |
| Production ratio of hydroxybutylphosphonic acid | 0 | 0 | 0 |

Comparative Example 3

The same procedure as in Example 1 was repeated, except that toluene was charged in an amount of 50 ml and n-butyraldehyde was not changed and the nitrogen gas was replaced by oxo gas (mixed gas of hydrogen: carbon monoxide=1:1 (mol ratio)) and the reaction mixture was maintained under a pressure of 5 kg/cm$^2$G at 90° C. The results are shown in the following Table.

| Reaction time | 1 | 4 |
|---|---|---|
| Remaining ratio of rhodium-phosphonate complex (%) | 21 | 0 |
| Production ratio of organic phosphonate (I) (%) | 79 | 100 |
| Production ratio of hydroxybutylphosphonic acid | 0 | 0 |

Reference Example 3

Preparation of Phosphonate (II)

About 200 ml of a toluene solution having 5.50 g(38.2 mmol) of α-naphthol and 3.47 g (43.9 mmol) of pyridine dissolved was dropwise added to about 1,000 ml of a toluene solution having 3.74 g (27.2 mmol) of phosphorus trichloride in a nitrogen atmosphere at 0° C. for about 2 hours under stirring. Thereafter, the reaction mixture was heated to 40° C., and was stirred for 0.5 hour, and was then cooled to room temperature. 300 ml of water was added to the resultant mixture, and the mixture was stirred for 0.5 hour. A toluene phase was obtained by separation, and was washed with water two times, and was dehydrated with anhydrous magnesium sulfate, and the toluene was distilled off. To the residue thus obtained, was added acetonitrile, and the solvent was distilled off again to fully remove toluene. The residue thus obtained was dried under reduced pressure to obtain 2.5 g of a thick malt syrup-like product. According to NMR analysis, the product contained 72.1 wt % of di-α-naphthylphosphonate, and further contained mono-α-naphthylphosphonate and starting α-naphthol. The product is referred to as "phosphonate (II)".

Examples 3 to 6 and Comparative Example 4

Into a stainless steel-made autoclave having an internal volume of 200 ml with up and down stirring system, was charged a solution having 19.7 mg (0.036 mmol) of di-μ-aceto-bis(1,5-cyclooctadiene)dirhodium ([Rh(C$_8$H$_{12}$)(μ-CH$_3$CO$_2$)]$_2$), 312.5 mg (0.292 mmol) of phosphite of the following formula and phosphonate dissolved in 60 ml of toluene, in a nitrogen atmosphere, and 4.53 g of propylene was further charged thereinto. The autoclave was heated to 70° C., and mixed gas of hydrogen:carbon monoxide=1:1 (mol ratio) was press-introduced thereinto up to 9.3 kg/cm$^2$G to start reaction. During the reaction, a mixed gas of hydrogen:carbon monoxide=1:1 (mol ratio) in a pressure reserver was supplied thereto by way of a pressure controller to maintain a constant pressure. The proceeding of the reaction was monitored by the pressure drop in the pressure reserver.

The autoclave was cooled to room temperature when the pressure drop in the pressure reserver was not observed. A gas and a liquid in the autoclave were measured by gas chromatography. The results are shown in the following Table 4.

Phosphite:

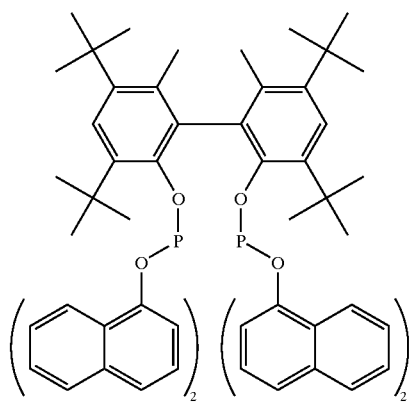

this result, absorption of gas stopped after 2.8 hours. The reaction performances were propylene conversion 98.1% and n/i ratio of the produced butyraldehyde=72.1. The propylene half-life was 14.8 minutes, and as compared with the result of Example 6, it was observed that there was a tendency of lowering a catalyst-poisoning function when the aldehyde was reacted with the phosphonate.

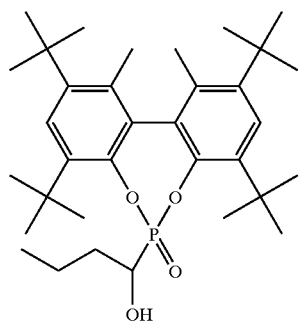

Example 7

The reaction was carried out in the same manner as in Example 3, except that the rhodium complex and phosphonate were replaced by 82.1 mg of rhodium-phosphonate complex prepared in Reference Example 2 and the phosphite amount was made 311.9 mg (0.291 mmol). As this result, the propylene conversion was 96.9%, the n/i ratio was 72.1 and the propylene half-life was 85.7 minutes, at the reaction time of 4.5 hours.

Examples 8 to 15 and Comparative Examples 5 and 6

Into a stainless steel-made autoclave having an internal volume of 200 ml with up and down stirring type, were charged 90 ml of mixed octene obtained by dimerization of butene, 10 ml of xylene, 12.6 mg (0.049 mmol) of rhodium dicarbonyl acetylacetonate, 632 mg (0.98 mmol) of tris(2, 4-di-t-butylphenyl)phosphite and phosphonate in a nitrogen

TABLE 4

| | Phosphonate | | | Reaction performances | | | |
|---|---|---|---|---|---|---|---|
| | | | | Propylene | | Propylene | Relative |
| | Kind | Amount (mg) | L/Rh *1 | Reaction time (hr) | reaction rate (%) | n/i *2 | half-period (min) *3 | activity *4 |
| Example 3 | I | 17.7 | 0.5 | 2.6 | 98.7 | 74.4 | 14.8 | 0.97 |
| Example 4 | II | 135.8 | 4.0 | 4.5 | 98.0 | 75.0 | 42.7 | 0.34 |
| Example 5 | II | 16.9 | 0.5 | 2.6 | 97.5 | 73.2 | 16.9 | 0.84 |
| Example 6 | I | 141.6 | 4.0 | 3.0 | 98.0 | 73.5 | 17.7 | 0.81 |
| Comparative Example 4 | — | — | 0 | 2.5 | 98.5 | 75.2 | 14.3 | 1.0 |

*1 Mol ratio of phosphonate to rhodium complex
*2 Ratio of n-butyraldehyde to isobutyraldehyde in product
*3 Calculated from pressure drop in pressure reserver
*4 Calculated from propylene half-life (Activity is estimated to be 1 when phosphonate is not added.)

Reference Example 4

Hydroformylation reaction was carried out in the same manner as in Example 6, except that the phosphonate (I) was replaced by 324.8 mg (mol ratio of phosphorus to rhodium=8) of the following hydroxybutylphosphonate (which is a reaction product of phosphonate (I) and butyraldehyde). As atmosphere. The autoclave was flushed with nitrogen, and was heated to 130° C. under stirring. A mixed gas of hydrogen: carbon monoxide=1:1 (mol ratio) was introduced up to 50 kg/cm$^2$G, and the reaction was carried out at 130° C. under a pressure of 50 kg/cm$^2$G for 30 minutes. The results are shown in the following Table 5.

TABLE 5

|  | Phosphonate | | | Octene |
|---|---|---|---|---|
| | Kind | Amount (mg) | P/Rh[*3] | conversion (%) |
| Example 8 | A[*1] | 45.5 | 2.0 | 20.9 |
| Example 9 | A | 22.6 | 1.0 | 40.3 |
| Example 10 | A | 17.0 | 0.75 | 47.5 |
| Example 11 | A | 11.3 | 0.5 | 50.2 |
| Example 12 | B[*2] | 28.5 | 2.2 | 41.9 |
| Example 13 | B | 13.3 | 1.0 | 44.7 |
| Example 14 | B | 7.7 | 0.58 | 45.5 |
| Example 15 | B | 3.7 | 0.28 | 49.5 |
| Comparative Example 5 | — | — | 0 | 53.1 |
| Comparative Example 6 | A | 2240 | 100 | 0[*4] |

[*1]Bis(2,4-di-t-butylphenyl)phosphonate
[*2]Mono(2,4-di-t-butylphenyl)phosphonate
[*3]Mol ratio of phosphonate to rhodium complex
[*4]Conversion after reacting for 5 hours was 0.

Reference Example 5

Preparation of Phosphonate from Phosphite

Into a stainless steel-made autoclave having an internal volume of 100 ml, was charged a solution having 16.2 mg of di-$\mu$-aceto-bis(1,5-cyclooctadiene)dirhodium complex and 260.1 mg of phosphite same as used in Example 1 dissolved in 50 ml of toluene. A mixed gas of hydrogen-:carbon monoxide=1:1 (mol ratio) was introduced thereinto up to 9 kg/cm$^2$G, and the resultant mixture was stirred at room temperature for 15 minutes to activate the catalyst, and the gas was discharged. Thereafter, the autoclave was flushed with nitrogen gas, and was heated at 130° C. for 136 hours. The autoclave was cooled, and the reaction solution was analyzed by high speed liquid chromatography, and as this result, it was observed that 61% of the charged phosphite was decomposed and that the following phosphonate was produced in an amount of 16 mol % to the phosphite.

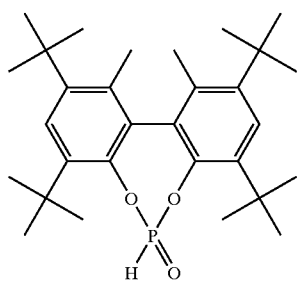

Example 16

Into a stainless steel-made autoclave having an internal volume of 200 ml with up and down stirring type, were charged 90 ml of mixed octene obtained by dimerization of butene, 10 ml of meta-xylene, 12.6 mg (0.049 mmol) of rhodium dicarbonylacetylacetonate and 44.7 mg (0.098 mmol) of phosphonate (No. 1 in Table 3) having the following formula in a nitrogen atmosphere. The autoclave was flushed with nitrogen, and was then heated to 130° C. under stirring. A mixed gas of hydrogen:carbon monoxide=1:1 (mol ratio) was introduced thereinto up to 50 kg/cm$^2$G, and reaction was carried out at 130° C. under a pressure of 50 kg/cm$^2$G for 5 hours, and conversion of starting material was 50.2%. Also, after the reaction, the reaction solution was homogeneous.

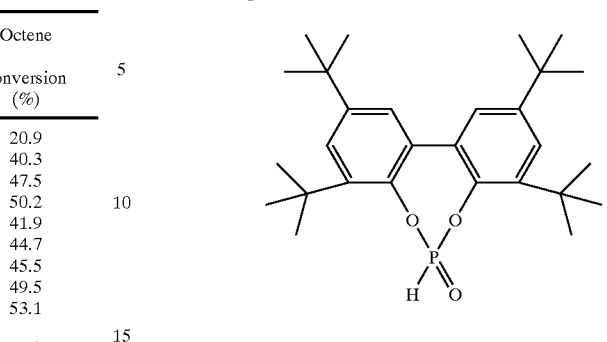

Example 17

Into a stainless steel-made autoclave having an internal volume of 200 ml with up and down stirring type, were charged 90 ml of mixed octene obtained by dimerization of butene, 10 ml of meta-xylene and 52.7 mg (0.049 mmol) of rhodium-phosphonate complex having the following structure in a nitrogen atmosphere. The autoclave was flushed with nitrogen, and was heated to 130° C. under stirring. A mixed gas of hydrogen:carbon Monoxide=1:1 (mol ratio) was introduced up to 50 kg/cm$^2$G, and reaction was carried out at 130° C. under a pressure of 50 kg/cm$^2$G for 5 hours, and as this result, conversion of the starting material was 52.2%. Also, after the reaction, the reaction solution was homogeneous.

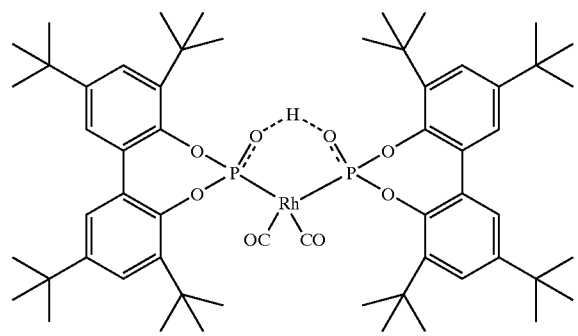

Comparative Example 7

The same procedure as in Example 16 was repeated, except that phosphonate was not added. As this result, conversion of the starting material was 34.5%. Also, after the reaction, the reaction solution contained a black rhodium metal deposit.

Example 18

Into a stainless steel-made autoclave having an internal volume of 200 ml with up and down stirring type, were charged 90 ml of mixed octene obtained by dimerization of butene, 10 ml of meta-xylene, 12.6 mg (0.049 mmol) of rhodium dicarbonylacetylacetonate, 31.9 mg (0.049 mmol) of tris(2,4-di-t-butylphenyl)phosphite and 22.5 mg (0.049 mmol) of phosphonate (No. 1 in Table 3) same as used in Example 16 in a nitrogen atmosphere. The autoclave was flushed with nitrogen, and was heated to 130° C. under stirring. A mixed gas of hydrogen:carbon monoxide=1:1 (mol ratio) was introduced thereinto up to 50 kg/cm$^2$G, and reaction was carried out at 130° C. under a pressure of 50 kg/cm²G for 5 hours, and as this result, conversion of the starting material was 67.3%. Also, after the reaction, the reaction solution was homogeneous.

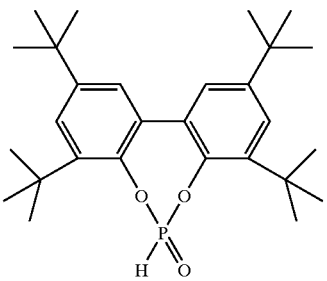

Example 19

Into a stainless steel-made autoclave having an internal volume of 200 ml with up and down stirring type, were charged 90 ml of mixed octene obtained by dimerization of butene, 10 ml of meta-xylene, 52.7 mg (0.049 mmol) of rhodium phosphonate complex same as used in Example 17 and 32.0 mg (0.049 mmol) of tris(2,4-di-t-butylphenyl) phosphite in a nitrogen atmosphere. The autoclave was substituted with nitrogen, and was heated to 130° C. under stirring. A mixed gas of hydrogen:carbon onoxide=1:1 (mol ratio) was introduced thereinto up to 50 kg/cm²G, and reaction was carried out at 130° C. under a pressure of 50 kg/cm²G for 5 hours, and as this result, conversion of starting material was 80.8%.

Also, after the reaction, the reaction solution was homogeneous.

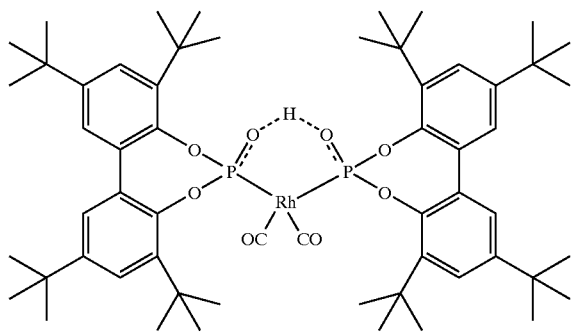

Comparative Example 8

The same procedure as in Example 18 was repeated, except that phosphonate was not added. As this result, conversion of the starting material 40.9%. Also, after the reaction, the reaction solution contained a black rhodium metal deposit.

The result of Examples 16 to 19 and Comparative Examples 7 to 8 are shown in the following Table 6.

TABLE 6

| | Phosphonate (P/Rh ratio) | Phosphite (P/Rh ratio) | Octene conversion (%) | Solution status after reaction |
|---|---|---|---|---|
| Example 16 | 2 *1 | 0 | 50.2 | No precipitation |
| Example 17 | 2 *2 | 0 | 52.2 | No precipitation |
| Comparative Example 7 | 0 | 0 | 34.5 | Precipitation of black deposit |
| Example 18 | 1 *1 | 1 | 67.3 | Precipitation of black deposit |
| Example 19 | 2 *2 | 1 | 80.8 | No precipitation |
| Comparative Example 8 | 0 | 1 | 40.9 | Precipitation of black deposit |

*1 Addition of Rh(acac) (CO)₂ and phosphonate
*2 Using phosphonate complex
Phosphite: tris(2,4-di-t-butylphenyl)phosphite H₂/CO 50 KG, 130° C. 5 hrs The present invention is based on the disclosures of Japanese Patent Applications No. 10-351117 and No. 10-354248.

What is claimed is:

1. A process for producing an aldehyde, which comprises a reaction step of producing an aldehyde by reacting an olefinic compound with carbon monoxide and hydrogen in the presence of a rhodium complex catalyst comprising at least rhodium and an organic phosphite in a reaction zone, a separation step of obtaining a catalyst solution containing the rhodium complex catalyst by separating the aldehyde from a reaction solution taken from the reaction zone, and a recycling step of recycling the catalyst solution into the reaction zone, wherein in said separation step, the aldehyde is removed from the reaction solution in an amount sufficient to leave aldehyde in the catalyst solution to be recycled in the recycling step, wherein the catalyst solution to be recycled has an aldehyde concentration of from 3 to 99 wt %, based on total catalyst solution.

2. The process according to claim 1, wherein the catalyst solution to be recycled has an aldehyde concentration of from 3.0 to 25 wt %, based on total catalyst solution.

3. The process according to claim 1, wherein the organic phosphite constituting the rhodium complex catalyst is expressed by the formula (1), $$P(OR^1)(OR^2)(OR^3) \tag{1}$$

wherein $R^1$ to $R^3$ are respectively independently a $C_1$–$C_{30}$ hydrocarbon group or a $C_5$–$C_{30}$ heteroaromatic hydrocarbon group, which may have a substituent.

4. The process according to claim 3, wherein $R^1$ to $R^3$ of the formula (1) are respectively independently a substituted aryl group expressed by the formula (2),

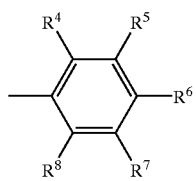

wherein $R^4$ is —$CR^9R^{10}R^{11}$ ($R^9$, $R^{10}$ and $R^{11}$ are respectively independently a hydrogen atom or a hydrocarbon group which may be fluorinated) or an aryl group which may have a substituent, $R^5$ to $R^8$ are respectively independently a hydrogen atom or an organic group selected from the group consisting of methyl, methoxy, tert-butyl and tert-amyl, wherein adjacent groups of $R^5$ to $R^8$ may be bonded to each other to form a condensed aromatic ring or a condensed heterocyclic ring.

5. The process according to claim 1, wherein the organic phosphite constituting the rhodium complex catalyst is expressed by the formula (3),

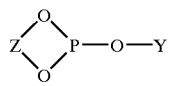
(3)

wherein Z is a divalent hydrocarbon group which may contain a hetero atom in a carbon chain and may have a substituent, and Y is a hydrocarbon group or a heteroaromatic hydrocarbon group, which may have a substituent.

6. The process according to claim 1, wherein the organic phosphite constituting the rhodium complex catalyst is expressed by the formula (9),

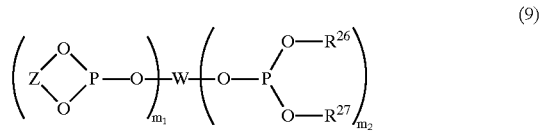
(9)

wherein Z is a divalent hydrocarbon group which may contain a hetero atom in a carbon chain and may have a substituent, $R^{26}$ and $R^{27}$ are respectively independently a $C_1$–$C_{30}$ hydrocarbon group or a $C_5$–$C_{30}$ heteroaromatic hydrocarbon group, which may have a substituent, W is a $(m_1+m_2)$ valent hydrocarbon group which may contain a hetero atom in a carbon chain and may have a substituent, and $m_1$ and $m_2$ are respectively an integer of 0 to 6, and $m^1+m_2=2$–6.

7. The process according to claim 6, wherein $R^{26}$ and $R^{27}$ of the formula (9) are respectively independently an aryl group which may have a substituent and W is expressed by the formula (10),

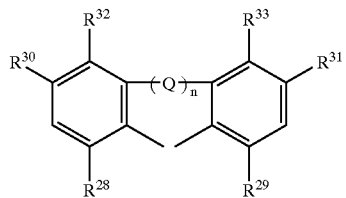

wherein $R^{28}$ and $R^{29}$ are respectively independently a $C_3$–$C_{20}$ branched alkyl group, $R^{30}$ and $R^{31}$ are respectively independently a $C_1$–$C_{20}$ alkyl or alkoxy group, $R^{32}$ and $R^{33}$ are respectively independently a hydrogen atom, a halogen atom, a silyl group, a siloxy group or a $C_1$–$C_{12}$ alkyl, cycloalkyl or alkoxy group, Q is a crosslinking group of —$CR^{15}R^{16}$—, —O—, —S—, —$NR^{17}$—, —$SiR^{18}R^{19}$— or —CO—, $R^{15}$ and $R^{16}$ of the crosslinking group are respectively independently a hydrogen atom, a $C_1$—$C_{12}$ alkyl group, a phenyl group, a tolyl group or an anisyl group, $R^{17}$ to $R^{19}$ are respectively independently a hydrogen atom or a methyl group, and n is 0 or 1.

8. The process according to claim 1, wherein the olefinic compound is selected from the group consisting of propylene, 1-butene, 2-butene, isobutene, mixed butene, 1-octene and mixed octene.

9. A process for producing an alcohol by directly hydrogenating the aldehyde obtained by the process according to claim 1 or by dimerizing the aldehyde and then hydrogenating.

10. A process for producing an aldehyde, which comprises a reaction step of producing an aldehyde by reacting an olefinic compound with carbon monoxide and hydrogen in the presence of a rhodium complex catalyst comprising at least rhodium and an organic phosphite in a reaction zone, a separation step of obtaining a catalyst solution containing the rhodium complex catalyst by separating the aldehyde from a reaction solution taken from the reaction zone, and a recycling step of recycling the catalyst solution into the reaction zone, wherein the catalyst solution to be recycled in the recycling step further contains an organic phosphonate of formula (a)

$$HP(O)(OX^1)(OX^2) \qquad (a)$$

in a molar ratio of organic phosphonate:rhodium (in the catalyst solution) of from 0.0001 to 5, wherein $X^1$ is hydrogen or a monovalent organic group, $X^2$ is a monovalent organic group, and $X^1$ and $X^2$ may be bonded to form a divalent organic group.

11. The process according to claim 10, wherein the catalyst is used by recycling for at least 6 months.

12. The process according to claim 10, wherein the organic phosphite constituting the rhodium complex catalyst is expressed by the formula (1), $$P(OR^1)(OR^2)(OR^3) \qquad (1)$$

wherein $R^1$ to $R^3$ are respectively independently a $C_1$–$C_{30}$ hydrocarbon group or a $C_5$–$C_{30}$ heteroaromatic hydrocarbon group, which may have a substituent.

13. The process according to claim 12, wherein $R^1$ to $R^3$ of the formula (1) are respectively independently a substituted aryl group expressed by the formula (2),

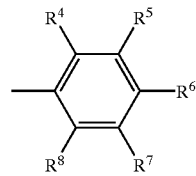

wherein $R^4$ is —$CR^9R^{10}R^{11}$ ($R^9$, $R^{10}$ and $R^{11}$ are respectively independently a hydrogen atom or a hydrocarbon group which may be fluorinated) or an aryl group which may have a substituent, $R^5$ to $R^8$ are respectively independently a hydrogen atom or an organic group selected from the group consisting of methyl, methoxy, tert-butyl and tert-amyl, wherein adjacent groups of $R^5$ to $R^8$ may be bonded to each other to form a condensed aromatic ring or a condensed heterocyclic ring.

14. The process according to claim 10, wherein the organic phosphite constituting the rhodium complex catalyst is expressed by the formula (3),

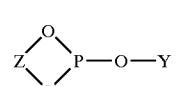
(3)

wherein Z is a divalent hydrocarbon group which may contain a hetero atom in a carbon chain and may have a substituent, and Y is a hydrocarbon group or a heteroaromatic hydrocarbon group, which may have a substituent.

15. The process according to claim 10, wherein the organic phosphite constituting the rhodium complex catalyst is expressed by the formula (9),

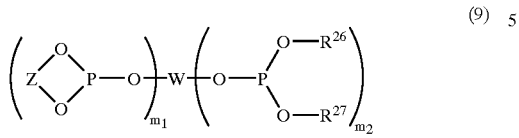

(9)

wherein Z is a divalent hydrocarbon group which may contain a hetero atom in a carbon chain and may have a substituent, $R^{26}$ and $R^{27}$ are respectively independently a $C_1$–$C_{30}$ hydrocarbon group or a $C_5$–$C_{30}$ heteroaromatic hydrocarbon group, which may have a substituent, W is a $(m_1+m_2)$ valent hydrocarbon group which may contain a hetero atom in a carbon chain and may have a substituent, and $m_1$ and $m_2$ are respectively an integer of 0 to 6, and $m_1+m_2=2$–6.

16. The process according to claim 15, wherein $R^{26}$ and $R^{27}$ of the formula (9) are respectively independently an aryl group which may have a substituent and W is expressed by the formula (10),

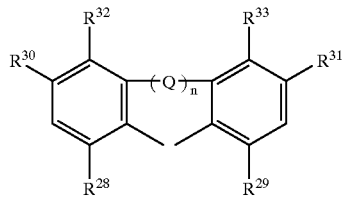

wherein $R^{28}$ and $R^{29}$ are respectively independently a $C_3$–$C_{20}$ branched alkyl group, $R^{30}$ and $R^{31}$ are respectively independently a $C_{-C20}$ alkyl or alkoxy group, $R^{32}$ and $R^{33}$ are respectively independently a hydrogen atom, a halogen atom, a silyl group, a siloxy group or a $C_1$–$C_{12}$ alkyl, cycloalkyl or alkoxy group, Q is a crosslinking group of —$CR^{15}R^{16}$—, —O—, —S—, —$NR^{17}$—, —$SiR^{18}R^{19}$— or —CO—, $R^{15}$ and $R^{16}$ of the crosslinking group are respectively independently a hydrogen atom, a $C_1$–$C_{12}$ alkyl group, a phenyl group, a tolyl group or an anisyl group, $R^{17}$ to $R^{19}$ are respectively independently a hydrogen atom or a methyl group, and n is 0 or 1.

17. The process according to claim 10, wherein the organic phosphonate is prepared from the organic phosphite in the reaction system.

18. The process according to claim 10, wherein the organic phosphonate is expressed by the formula (11),

(11)

wherein Z is a divalent hydrocarbon group which may contain a hetero atom in a carbon chain and may have a substituent.

19. The process according to claim 10, wherein the organic phosphonate is expressed by the formula (12) or (13),

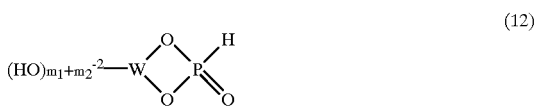

(12)

wherein W is a divalent hydrocarbon group which may contain a hetero atom in a carbon chain and may have a substituent, and $m_1+m_2$ is an integer of from 2 to 6, and

(13)

wherein $R^{26}$ and $R^{27}$ are respectively independently a $C_1$–$C_{30}$ hydrocarbon group or a $C_5$–$C_{30}$ heteroaromatic hydrocarbon group, which may have a substituent.

20. The process according to claim 10, wherein the molar ratio of organic phosphonate:rhodium (in the catalyst solution) is from 0.01 to 1.5.

21. The process according to claim 10, wherein the olefinic compound is selected from the group consisting of propylene, 1-butene, 2-butene, isobutene, mixed butene, 1-octene and mixed octene.

22. A process for producing an alcohol by directly hydrogenating the aldehyde obtained by the process according to claim 10 or by dimerizing and then hydrogenating.

* * * * *